US012662548B2

(12) United States Patent　　(10) Patent No.:　US 12,662,548 B2
Fujita et al.　　(45) Date of Patent:　*Jun. 23, 2026

(54) METHOD FOR TREATING CANCER BY ADMINISTRATION OF ANTIBODIES THAT BIND TO EXTRACELLULAR REGION PORTION OF MCEMP1 PROTEIN

(71) Applicant: TORAY INDUSTRIES, INC., Tokyo (JP)

(72) Inventors: Takayuki Fujita, Kamakura (JP); Fumiyoshi Okano, Kamakura (JP)

(73) Assignee: TORAY INDUSTRIES, INC., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/960,354

(22) Filed: Oct. 5, 2022

(65) Prior Publication Data

US 2023/0030982 A1　　Feb. 2, 2023

Related U.S. Application Data

(63) Continuation of application No. 16/088,502, filed as application No. PCT/JP2017/012239 on Mar. 27, 2017, now Pat. No. 11,492,410.

(30) Foreign Application Priority Data

Mar. 28, 2016　(JP) ................................. 2016-064035

(51) Int. Cl.
| | |
|---|---|
| *C07K 16/28* | (2006.01) |
| *A61K 38/00* | (2006.01) |
| *A61K 39/395* | (2006.01) |
| *A61K 45/00* | (2006.01) |
| *A61K 45/06* | (2006.01) |
| *A61P 35/00* | (2006.01) |
| *C07K 16/30* | (2006.01) |
| *A61K 39/00* | (2006.01) |
| *C12N 15/09* | (2006.01) |

(52) U.S. Cl.
CPC .............. *C07K 16/30* (2013.01); *A61K 38/00* (2013.01); *A61K 39/39558* (2013.01); *A61K 45/00* (2013.01); *A61K 45/06* (2013.01); *A61P 35/00* (2018.01); *C07K 16/28* (2013.01); *A61K 2039/505* (2013.01); *C07K 2317/732* (2013.01); *C12N 15/09* (2013.01)

(58) Field of Classification Search
None
See application file for complete search history.

(56) References Cited

U.S. PATENT DOCUMENTS

| | | | |
|---|---|---|---|
| 2005/0288487 A1 | 12/2005 | Li et al. | |
| 2015/0005361 A1* | 1/2015 | Slukvin .............. | G01N 33/5044 |
| | | | 506/10 |

FOREIGN PATENT DOCUMENTS

| | | | |
|---|---|---|---|
| JP | 2003-513610 A | | 4/2003 |
| JP | 2005-528087 A | | 9/2005 |
| KR | 10-2010-0121949 A | | 11/2010 |
| WO | WO 00/55180 A2 | | 9/2000 |
| WO | WO 03/057252 A1 | | 7/2003 |
| WO | WO 2011/144718 A2 | | 11/2011 |

OTHER PUBLICATIONS

Hjelm et al (Plos One, 2012, vol. 7, issue 12; e45817, internet pp. 1-12).*
He et al (PNAS, 2016, 113:11931-11936, IDS).*
Weitzman et al (Leukemia & Lymphoma, 2009, 50:1361-1368, IDS).*
Atlas Antibodies—Anti-MCEMP1 Antibody HPA014731, printed Nov. 2024 (https://www.atlasantibodies.com/products/primary-antibodies/triple-a-polyclonals/anti-mcemp1-antibody-hpa014731-100ul/?language=en).*
Abcam product # ab121447, printed Nov. 2024 (https://www.abcam.com/en-us/products/primary-antibodies/mcemp1-antibody-ab121447#application=wb).*
Thermo Fisher #PA5-53223, printed Nov. 2024 (https://www.thermofisher.com/antibody/product/MCEMP1-Antibody-Polyclonal/PA5-53223).*
Database WPI Week 201152, Thomson Scientific, London, GB; AN 2010-Q33578, XP002794675, & KR 2010 0121949 A (Korea Res Inst Bioscience & BIOTECHNOLOGY) Nov. 19, 2010 (Nov. 19, 2010) * abstract *.
Extended European Search Report issued Oct. 11, 2019, in European Patent Application No. 17774859.7.
He et al., "Epitope specificity plays a critical role in regulating antibody-dependent cell-mediated cytotoxicity against influenza A virus," PNAS (2016), vol. 113, pp. 11931-11936.
International Search Report, issued in PCT/JP2017/012239, dated May 9, 2017.

(Continued)

*Primary Examiner* — Laura B Goddard

(74) *Attorney, Agent, or Firm* — Birch, Stewart, Kolasch & Birch, LLP

(57) ABSTRACT

An object of the present invention is to identify cancer antigen proteins specifically expressed on the surface of cancer cells and to provide a use of antibodies targeting such proteins as therapeutic and/or preventive agents for cancer. The present invention relates to, for example, a pharmaceutical composition for treatment and/or prevention of a cancer, which comprises, as an active ingredient, an antibody or fragment thereof having an immunological reactivity with an MCEMP1 protein having an amino acid sequence shown in any one of the even numbered SEQ ID NOS: 2 to 8 or an amino acid sequence having 80% or more sequence identity with the amino acid sequence, or with a fragment of the MCEMP1 protein comprising 7 or more consecutive amino acids.

2 Claims, 4 Drawing Sheets

Specification includes a Sequence Listing.

(56)            References Cited

OTHER PUBLICATIONS

Li et al., "Identification and expression of a new type II transmembrane protein in human mast cells," Genomics (2005), vol. 86, pp. 68-75.
Weitzman et al., "Variable Contribution of Monoclonal Antibodies to ADCC in patients with chronic lymphocytic leukemia," Leukemia & Lymphoma (2009). vol. 50. pp. 1361-1368.
Written Opinion of the International Searching Authority, issed in PCT/JP2017/012239, dated May 9, 2017.

* cited by examiner

Breast cancer 1

Neuroblastoma 1

Breast cancer 2

Neuroblastoma 2

Melanoma

Leukemia

Thymoma

SEQUENCE LISTING

Sequence total quantity: 30
SEQ ID NO: 1          moltype = DNA   length = 1326
FEATURE               Location/Qualifiers
source                1..1326
                      mol_type = unassigned DNA
                      organism = Homo sapiens
CDS                   26..589
SEQUENCE: 1
tggacaaatt tgcgggctgg ggaccatgga agtggaggaa atctacaagc accaggaagt   60
caagatgcaa gcaccagcct tcagggacaa gaaacagggg gtctcagcca agaatcaagg  120
tgcccatgac ccagactatg agaatatcac cttggccttc aaaaatcagg accatgcaaa  180
gggtggtcat tcacgaccca cgagccaagt cccagcccag tgcaggccgc cctcagactc  240
cacccaggtc ccctgctggt tgtacagagc catcctgagc ctgtacatcc tcctggccct  300
ggcctttgtc ctctgcatca tcctgtcagc cttcatcatg gtgaagaatg ctgagatgtc  360
caaggagctg ctgggcttta aaagggagct ttggaatgtc tcaaactccg tacaagcagt  420
cgaagagaga cagaagagag gctgggattc cgttcagcag agcatcacca tggtcaggag  480
caagattgat agattagaga cgacattagc aggcataaaa aacattgaca caaaggtaca  540
gaaaatcttg gaggtgctgc agaaaatgcc acagtcctca cctcaataaa tgagaggaca  600
ttgtggcagc caaagccaca acttggaaga tggggctgca cctgccaacg aagacgggaa  660
atgacccccc ccccccagcc tagtgtgaac ctgcccctcg tcccacgtat agaaaaacct  720
cgagtcatgg tgaatgagtg tctcggagtt gctcgtgtgt gtgtacacct gcgtgcgtgt  780
gtgtgcgtgt gtgcgcgtgt gttcgtgtat gtgcgtgtgt gcgtgcgcgt gtgtgtgcat  840
tttgcaaagg gtggacattt cagtgtatct cccagaaagg tgatgaatga ataggactga  900
gagtcacagt gaatgtggca tgcatgcctg tgtcatgtga catatgtgag tctcggcatg  960
tcacggtggg tggctgtgtc tgagcacctc cagcagatgt cactctgagt gtgggtgttg 1020
gtgacatgca ttgcacgggc ctgtctccct gtttgtgtaa acatactaga gtatactgcg 1080
gcgtgttttc tgtctaccca tgtcatggtg ggggagattt atctccgtac atgtgggtgt 1140
cgccatgtgt gccctgtcac tatctgtggc tgggtgaacg gctgtgtcat tatgagtgtg 1200
ccgagttatg ccacctgtg tgctcagggc acatgcacac agacatttat ctctgcactc 1260
acattttgtg acttatgaag ataaataaag tcaaggggaaa acagcgtcaa aaaaaaaaaa 1320
aaaaaa                                                            1326

SEQ ID NO: 2          moltype = AA   length = 187
FEATURE               Location/Qualifiers
source                1..187
                      mol_type = protein
                      organism = Homo sapiens
SEQUENCE: 2
MEVEEIYKHQ EVKMQAPAFR DKKQGVSAKN QGAHDPDYEN ITLAFKNQDH AKGGHSRPTS   60
QVPAQCRPPS DSTQVPCWLY RAILSLYILL ALAFVLCIIL SAFIMVKNAE MSKELLGFKR  120
ELWNVSNSVQ ACEERQKRGW DSVQQSITMV RSKIDRLETT LAGIKNIDTK VQKILEVLQK  180
MPQSSPQ                                                             187

SEQ ID NO: 3          moltype = DNA   length = 1124
FEATURE               Location/Qualifiers
source                1..1124
                      mol_type = unassigned DNA
                      organism = Canis familiaris
CDS                   66..689
SEQUENCE: 3
ctcatctgcc atgacacctt ccggtgggtg gggatgtgtg tgggtaaact ggcccactgg   60
gaaccatgga gtctgaggaa atctacacga atcagaaggt cgagatgcag gcagccttca  120
aagacaagaa acagagggtc ccagctgata aggaaggtgc agataaccct gactatgaga  180
atatcacctt ggccttgaga aaccaggacc agccaaaggg cagccattta ccacccaaga  240
atcagagcaa gcagccacct gccaggacac atcacacggc cttgggaggg gcccacgtcc  300
caaccctgtc taggctgccc tcagactctg gccagctccc ccgttgtctg cacagagtca  360
tcatgagcct gtacatgctc ctcgccctgt cctgcatcat tctcttagtc ttggtcctca  420
tgaagaatct ggagatgtcc caggagttgc tggccctgaa aagggagctc tggaatgtgt  480
ccgtctcggt gcaagagtgc caggagcagc agaatcaggg ctggagcacc gtccggcagc  540
tcctggtgga ggccaagcgt gacatttcca tggtcggag aaatgcccag cttgcgagtg  600
agaaggtgaa gacgctgaca gcagacataa gccatatcaa gagtaagtta caggaaatct  660
ccaagatgct ggagaagcca aagccataga cctcaacata cgcgaggaca tcgaagccct  720
ggctgcagct tggcggacgg ggctgcgcct cccagtgaag atggccacgt gtgtgcacca  780
cgtgtgttgc gagcctaagg cgtgacacag tgggtggctg tgtcagcagg gaccacgaaa  840
gtgtgtcagc gtgttgttgg cagcatgtgt agcaccgtga ctgtcctgtg  900
gtatgttgtg tgtaaatgtg tcacggcaga gccgtggcgg gggcacccca cgtgtcactg  960
taattgtggg tgccctgtca ctacctgtgt tggtgtgaac aggtgtctgc caacgagcga 1020
ctgaggatgt cacggagggg gttcggagca tgtacacatg tatgtccatt tgttcccgcg 1080
ctcacgttgt gtgatttgtg aagataaagg ccgatggaaa agaa                   1124

SEQ ID NO: 4          moltype = AA   length = 207
FEATURE               Location/Qualifiers
source                1..207
                      mol_type = protein
                      organism = Canis familiaris
SEQUENCE: 4
MESEEIYTNQ KVEMQAAFKD KKQRVPADKE GADNPDYENI TLAFRNQDQP KGSHLPPKNQ   60
SKQPPARTHH TALGGAHVPT LSRLPSDSGQ LPRCLHRVIM SLYMLLALSC IILLVLVLMK  120

```
NLEMSQELLA LKRELWNVSV SVQECQEQQN QGWSTVRQLL VEAKRDISMV GRNAQLASEK   180
VKTLTADISH IKSKLQEISK MLEKPKP                                       207

SEQ ID NO: 5              moltype = DNA  length = 1416
FEATURE                   Location/Qualifiers
source                    1..1416
                          mol_type = unassigned DNA
                          organism = Felis catus
CDS                       24..641
SEQUENCE: 5
tctgcttgaa tcaggaggtc aggatgcaag cagcagactt caaaggcaag aaacagaggg   60
ccccagacca taaggaaggt tcggtacctc aaggtgcaga ccctgactat gagaatatca   120
ccttgacctt cagaaaccag gagcaaccaa ggggcagcca ttcaccaccc aagaatcgag   180
gcaagcagcc acctgccagc ccgcacctca cagcctcagg agggcccct gtcccagcct   240
ggtcgaagca ggcccagac tctgcccagg tccctcgttg gctgcacaga gtcaccctga   300
gcctgtacat cctccttgcc ctgttctgca tcgttctctt ggccttggtc ctggtgaaga   360
attctgaggt gtcccaggag ctgctggtcg tgaaaaggga gctccagaat gtctccatct   420
cgggacaaca gtgtcaggag gagcagaaac agggctggag cagcgtccag cagctcatca   480
cggaggccag gcaggacatt gacatgatca agagaaatgt ccacatcggg aacgagaaag   540
tgaagacgct gtcaacagac ttaagccaaa tcaagactaa attacatgaa atctccaaga   600
tactagaaa gaagccgcag ccacagccca cagctcaata aatgagaaga cattgacacc   660
caggctgcag cttggaggac ggggctgcac ttccccgtga agacggccgc atgtgtgcct   720
catggtgtca cgggagcgat aacacatgat acagtgggcg gctgtgtcag caaggaccgc   780
agaagtgtgt cagcctgggc gcgggtgttg gtaacacgtg ttgcactgtg aacacgtgtg   840
aatgtcctgt ggtatgttgt gtgtgaatgt catggagctg tgtgtgtgtg tgcgcgtgcg   900
tgtgtgtgtg tggagcaccc cctacatcac tgtaactgcg ggtgttgagg gtgtaccccg   960
tcactccctg tgttgtgtga acaggtgggg gtcagtgtgt gactgattat gtcaccgagg   1020
gtgtgcagag cgggtacatt tgtgcgttcc cttgtttctg cactcacgtt ttgtgatttg   1080
tgacgataaa ggccaatggg aaagaatgtg gctttcagat ctgttcctgg gagcatctgg   1140
gggtgggggt ggggaccggg tggcggaggg tctgcaaagta ttaagggatg aggaaagtca   1200
cacagcaagc acgcggacgt gataaccagg agccctgggg gcacgagtgt gtgtgagcat   1260
gaatgccctg aatgggtcct tttgtgccca tgaacttgta cccagcaagg aacagtctcc   1320
gtgtctgaga ctgtgtgccc agcagggttt gtggcccgag atatacactg tttccctaag   1380
tggggctcct gggtggctca gtcggttaag cgtccg                            1416

SEQ ID NO: 6              moltype = AA  length = 205
FEATURE                   Location/Qualifiers
source                    1..205
                          mol_type = protein
                          organism = Felis catus
SEQUENCE: 6
MQAADFKGKK QRAPDHKEGS VPQGADPDYE NITLTFRNQE QPRGSHSPPK NRGKQPPASP   60
HLTASGGAPV PAWSKQAPDS AQVPRWLHRV TLSLYILLAL FCIVLLALVL VKNSEVSQEL   120
LVVKRELQNV SISGQQCQEE QKQGWSSVQQ LITEARQDID MIKRNVHIGN EKVKTLSTDL   180
SQIKTKLHEI SKILEKKPQP QPTAQ                                         205

SEQ ID NO: 7              moltype = DNA  length = 1132
FEATURE                   Location/Qualifiers
source                    1..1132
                          mol_type = unassigned DNA
                          organism = Mus musculus
CDS                       21..572
SEQUENCE: 7
acgtgaatca accaagcaga atgcatgcat cagcctccca ggataagaac cggaggaagc   60
caggtcatga tgaaggtgct cacaatcctg actacgagga tataaccttg gccttcagaa   120
acaaggacca actcaaactc agccaatcaa cacccacaaa acaagccaag ttcaagacat   180
ccctggaccc agctgagtcc ccgccttggt tgtacagaac cattatgatg ttgtatgttc   240
tccttgctct cgtctttta tcctgcatcg tcctctctgc tttggtcttg gtgaaaaatt   300
ctgagatgtc caaggagctg tggaccttga aagcagagct ttcgaatgtt tcagacacgg   360
tgtggaatat ccgggagctc cagaatcagc aaacgacggt ttgggaagct gcccagggag   420
acatcaagga ggtcaagaag acccttggca cagtcatgag tagcatccag actggaaacg   480
accggctgaa gactgtgccg gcagatataa cccaaatcaa gaaaactctt gaggcgctag   540
aaaagaaggc acagcctcag cccagtacat aagaggacac cacagcagta cctgtgaaga   600
ctccgaattg cacctgctag tgaagatggc agatggggt ggggtactgag cttgagtgtg   660
aacctgccgt gcatcctcat ataaaaaaga ttctccacca gggggaatga gtgttgaaga   720
ggtgtgtatg caaatgagca tttggggttt ccatgtattc caggagaagg gtttatggtg   780
gaaagagaac atggcagtca cagcaggtgt tactctttat gggccacata ggtgtatgcc   840
ctggcttatg tgagtatagg catgtcctgg ttggcagcta ttcccgagaa gtccccaaag   900
tgtaagtgac atgtaggaca tgcctcccca ttctcttgct catgtatgtg catctggctg   960
ttctgtatgt gtgtcactga agtggtgggt gatagacatc accctggaga tgtgtcatgg   1020
catgggtcat tcctagtgtt tttggtcatg tcagcttgtg tgttcagggc atgcacacaa   1080
atgtagccat cgatttctgc acttgtattt atgattcaag aagataaatg cc           1132

SEQ ID NO: 8              moltype = AA  length = 183
FEATURE                   Location/Qualifiers
source                    1..183
                          mol_type = protein
                          organism = Mus musculus
SEQUENCE: 8
```

```
MHASASQDKN RRKPGHDEGA HNPDYENITL AFRNKDQLKL SQSTPTKQAK FKTSLDPAES    60
PPWLYRTIMM LYVLLALVFL SCIVLSALVL VKNSEMSKEL WTLKAELSNV SDTVWNIREL   120
QNQQTRIWEA AQGDIKEVKK TLGTVMSSIQ TGNDRLKTVP ADITQIKKTL EALEKKAQPQ   180
PST                                                                183

SEQ ID NO: 9            moltype = DNA  length = 249
FEATURE                 Location/Qualifiers
source                  1..249
                        mol_type = unassigned DNA
                        organism = Homo sapiens
CDS                     1..249
SEQUENCE: 9
gtgaagaatg ctgagatgtc caaggagctg ctgggcttta aaagggagct ttggaatgtc    60
tcaaactccg tacaagcatg cgaagagaga cagaagagag gctgcggatc cgttcagcag   120
agcatcacca tggtcaggag caagattgat agattagaga cgacattagc aggcataaaa   180
aacattgaca caaaggtaca gaaaatcttg gaggtgctgc agaaaatgcc acagtcctca   240
cctcaataa                                                           249

SEQ ID NO: 10           moltype = AA  length = 82
FEATURE                 Location/Qualifiers
source                  1..82
                        mol_type = protein
                        organism = Homo sapiens
SEQUENCE: 10
VKNAEMSKEL LGFKRELWNV SNSVQACEER QKRGWDSVQQ SITMVRSKID RLETTLAGIK    60
NIDTKVQKIL EVLQKMPQSS PQ                                             82

SEQ ID NO: 11           moltype = DNA  length = 267
FEATURE                 Location/Qualifiers
source                  1..267
                        mol_type = unassigned DNA
                        organism = Canis familiaris
CDS                     1..267
SEQUENCE: 11
aagaatctgg agatgtccca ggagttgctg gccctgaaaa gggagctctg gaatgtgtcc    60
gtctcggtgc aagagtgcca ggagcagcag aatcagggct ggagcaccgt ccggcagctc   120
ctggtggagg ccaagcgtga catttccatg gtcgggagaa atgcccagct tgcgagtgag   180
aaggtgaaga cgctgacagc agacataagc catatcaaga gtaagttaca ggaaatctcc   240
aagatgctgg agaagccaaa gccatag                                       267

SEQ ID NO: 12           moltype = AA  length = 88
FEATURE                 Location/Qualifiers
source                  1..88
                        mol_type = protein
                        organism = Canis familiaris
SEQUENCE: 12
KNLEMSQELL ALKRELWNVS VSVQECQEQQ NQGWSTVRQL LVEAKRDISM VGRNAQLASE    60
KVKTLTADIS HIKSKLQEIS KMLEKPKP                                       88

SEQ ID NO: 13           moltype = DNA  length = 285
FEATURE                 Location/Qualifiers
source                  1..285
                        mol_type = unassigned DNA
                        organism = Felis catus
CDS                     1..285
SEQUENCE: 13
aagaattctg aggtgtccca ggagctgctg gtcgtgaaaa gggagctcca gaatgtctcc    60
atctcgggac aacagtgtca ggaggagcag aaacagggct ggagcagcgt ccagcagctc   120
atcacggagg ccaggcagga cattgacatg atcaagagaa atgtccacat cgggaacgag   180
aaagtgaaga cgctgtcaac agacttaagc caaatcaaga ctaaattaca tgaaatctcc   240
aagatactag agaagaagcc gcagccacag cccacagctc aataa                   285

SEQ ID NO: 14           moltype = AA  length = 94
FEATURE                 Location/Qualifiers
source                  1..94
                        mol_type = protein
                        organism = Felis catus
SEQUENCE: 14
KNSEVSQELL VVKRELQNVS ISGQQCQEEQ KQGWSSVQQL ITEARQDIDM IKRNVHIGNE    60
KVKTLSTDLS QIKTKLHEIS KILEKKPQPQ PTAQ                                94

SEQ ID NO: 15           moltype = DNA  length = 279
FEATURE                 Location/Qualifiers
source                  1..279
                        mol_type = unassigned DNA
                        organism = Mus musculus
CDS                     1..279
SEQUENCE: 15
aaaaattctg agatgtccaa ggagctgtgg accttgaaag cagagctttc gaatgtttca    60
```

```
gacacggtgt ggaatatccg ggagctccag aatcagcaaa cgaggatttg ggaagctgcc    120
caggggggaca tcaaggaggt caagaagacc cttggcacag tcatgagtag catccagact    180
ggaaacgacc ggctgaagac tgtgccggca gatataaccc aaatcaagaa aactcttgag    240
gcgctagaaa agaaggcaca gcctcagccc agtacataa                           279

SEQ ID NO: 16              moltype = AA   length = 92
FEATURE                    Location/Qualifiers
source                     1..92
                           mol_type = protein
                           organism = Mus musculus
SEQUENCE: 16
KNSEMSKELW TLKAELSNVS DTVWNIRELQ NQQTRIWEAA QGDIKEVKKT LGTVMSSIQT    60
GNDRLKTVPA DITQIKKTLE ALEKKAQPQP ST                                  92

SEQ ID NO: 17              moltype = DNA   length = 20
FEATURE                    Location/Qualifiers
misc_feature               1..20
                           note = T3 primer
source                     1..20
                           mol_type = other DNA
                           organism = synthetic construct
SEQUENCE: 17
aattaaccct cactaaaggg                                                20

SEQ ID NO: 18              moltype = DNA   length = 19
FEATURE                    Location/Qualifiers
misc_feature               1..19
                           note = T7 primer
source                     1..19
                           mol_type = other DNA
                           organism = synthetic construct
SEQUENCE: 18
taatacgact cactatagg                                                 19

SEQ ID NO: 19              moltype = DNA   length = 20
FEATURE                    Location/Qualifiers
misc_feature               1..20
                           note = canis RT primer sense
source                     1..20
                           mol_type = other DNA
                           organism = synthetic construct
SEQUENCE: 19
ccacgtccca accctgtcta                                                20

SEQ ID NO: 20              moltype = DNA   length = 20
FEATURE                    Location/Qualifiers
misc_feature               1..20
                           note = canis RT primer antisense
source                     1..20
                           mol_type = other DNA
                           organism = synthetic construct
SEQUENCE: 20
gtgctccagc cctgattctg                                                20

SEQ ID NO: 21              moltype = DNA   length = 20
FEATURE                    Location/Qualifiers
misc_feature               1..20
                           note = human RT primer sense
source                     1..20
                           mol_type = other DNA
                           organism = synthetic construct
SEQUENCE: 21
tggccttcaa aaatcaggac                                                20

SEQ ID NO: 22              moltype = DNA   length = 21
FEATURE                    Location/Qualifiers
misc_feature               1..21
                           note = human RT primer antisense
source                     1..21
                           mol_type = other DNA
                           organism = synthetic construct
SEQUENCE: 22
aggctcagga tggctctgta c                                              21

SEQ ID NO: 23              moltype = DNA   length = 20
FEATURE                    Location/Qualifiers
misc_feature               1..20
                           note = mouse RT primer sense
source                     1..20
```

```
                        mol_type = other DNA
                        organism = synthetic construct
SEQUENCE: 23
tccaaggagc tgtggacctt                                            20

SEQ ID NO: 24          moltype = DNA   length = 20
FEATURE                Location/Qualifiers
misc_feature           1..20
                        note = mouseRT primer antisense
source                 1..20
                        mol_type = other DNA
                        organism = synthetic construct
SEQUENCE: 24
agtcttcagc cggtcgtttc                                            20

SEQ ID NO: 25          moltype = DNA   length = 39
FEATURE                Location/Qualifiers
misc_feature           1..39
                        note = human MCEMP1 EcoRI primer sense
source                 1..39
                        mol_type = other DNA
                        organism = synthetic construct
SEQUENCE: 25
gaattcgccg ccaccatgga agtggaggaa atctacaag                       39

SEQ ID NO: 26          moltype = DNA   length = 29
FEATURE                Location/Qualifiers
misc_feature           1..29
                        note = human MCEMP1 NotI primer antisense
source                 1..29
                        mol_type = other DNA
                        organism = synthetic construct
SEQUENCE: 26
gcggccgctt attgaggtga ggactgtgg                                  29

SEQ ID NO: 27          moltype = DNA   length = 28
FEATURE                Location/Qualifiers
misc_feature           1..28
                        note = human MCEMP1ECD KpnI primer sense
source                 1..28
                        mol_type = other DNA
                        organism = synthetic construct
SEQUENCE: 27
ggtaccaaga atgctgagat gtccaagg                                   28

SEQ ID NO: 28          moltype = DNA   length = 27
FEATURE                Location/Qualifiers
misc_feature           1..27
                        note = human MCEMP1ECD EcoRI primer antisense
source                 1..27
                        mol_type = other DNA
                        organism = synthetic construct
SEQUENCE: 28
gaattcggtt gaggtgagga ctgtggc                                    27

SEQ ID NO: 29          moltype = DNA   length = 960
FEATURE                Location/Qualifiers
misc_feature           1..960
                        note = Fc fusion protein
source                 1..960
                        mol_type = other DNA
                        organism = synthetic construct
CDS                    1..960
SEQUENCE: 29
aagaatgctg agatgtccaa ggagctgctg ggctttaaaa gggagctttg gaatgtctca   60
aactccgtac aagcatgcga agagagacag aagagaggct gggattccgt tcagcagagc  120
atcaccatgg tcaggagcaa gattgataga ttagagacga cattagcagg cataaaaaac  180
attgacacaa aggtacagaa aatcttggag gtgctgcaga aaatgccaca gtcctcacct  240
caaccgaatt ctgcagatat ccccagaggg cccacaatca agccctgtcc tccatgcaaa  300
tgcccagcac ctaacctctt gggtggacca tccgtcttca tcttccctcc aaagatcaag  360
gatgtactca tgatctccct gagccccata gtcacatgtg tggtggtgga tgtgagcgag  420
gatgacccag atgtccagat cagctggttt gtgaacaacg tggaagtaca cacagctcag  480
acacaaaccc atagagagga ttacaacagt actctccggg tggtcagtgc cctccccatc  540
cagcaccagg actggatgag tggcaaggag ttcaaatgca aggtcaacaa caaagacctc  600
ccagcgccca tcgagagaac catctcaaaa cccaaagggt cagtaagagc tccacaggta  660
tatgtcttgc ctccaccaga agaagagatg actaagaaac aggtcactct gacctgcatg  720
gtcacagact tcatgcctga agacatttac gtggagtgga ccaacaacgg gaaaacagag  780
ctaaactaca agaacactga accagtcctg gactctgatg gttcttactt catgtacagc  840
aagctgagag tggaaaagaa gaactgggtg gaaagaaata gctactcctg ttcagtggtc  900
```

-continued

```
cacgagggtc tgcacaatca ccacacgact aagagcttct cccggactcc gggtaaatga   960

SEQ ID NO: 30            moltype = AA  length = 319
FEATURE                  Location/Qualifiers
REGION                   1..319
                         note = Fc fusion protein
source                   1..319
                         mol_type = protein
                         organism = synthetic construct
SEQUENCE: 30
KNAEMSKELL GFKRELWNVS NSVQACEERQ KRGWDSVQQS ITMVRSKIDR LETTLAGIKN   60
IDTKVQKILE VLQKMPQSSP QPNSADIPRG PTIKPCPPCK CPAPNLLGGP SVFIFPPPKIK  120
DVLMISLSPI VTCVVVDVSE DDPDVQISWF VNNVEVHTAQ TQTHREDYNS TLRVVSALPI   180
QHQDWMSGKE FKCKVNNKDL PAPIERTISK PKGSVRAPQV YVLPPPEEEM TKKQVTLTCM   240
VTDFMPEDIY VEWTNNGKTE LNYKNTEPVL DSDGSYFMYS KLRVEKKNWV ERNSYSCSVV   300
HEGLHNHHTT KSFSRTPGK                                                319
```

1

METHOD FOR TREATING CANCER BY ADMINISTRATION OF ANTIBODIES THAT BIND TO EXTRACELLULAR REGION PORTION OF MCEMP1 PROTEIN

CROSS-REFERENCE TO RELATED APPLICATIONS

This application is a continuation of U.S. application Ser. No. 16/088,502 filed on Sep. 26, 2018, which is the National Phase of PCT International Application No. PCT/JP2017/012239, filed on Mar. 27, 2017, which claims priority 35 U.S.C. § 119(a) to Patent Application No. 2016-064035, filed in Japan on Mar. 28, 2016, all of which are hereby expressly incorporated by reference into the present application.

REFERENCE TO ELECTRONIC SEQUENCE LISTING

This application contains a Sequence Listing which has been submitted electronically in .XML format and is hereby incorporated by reference in its entirety. Said .XML copy, created on Sep. 15, 2022, is named "PH-6864-PCT-US-C1.xml" and is 42,063 bytes in size. The sequence listing contained in this .XML file is part of the specification and is hereby incorporated by reference herein in its entirety.

TECHNICAL FIELD

The present invention relates to a novel medical use of antibodies to MCEMP1 or fragments thereof as, for example, therapeutic and/or preventive agents for cancer.

BACKGROUND ART

In recent years, a variety of antibody medicines for cancer treatment that target antigen proteins on cancer cells have come into existence. The antibody medicines used as cancer-specific therapeutic agents exhibit drug efficacy to a certain extent, and thus they have been gaining attention. However, many of target antigen proteins are also expressed on multiple normal cells. As a result of antibody administration, not only cancer cells, but also normal cells on which a target antigen has been expressed can be damaged, thereby causing a side effect, which becomes problematic. Hence, it is expected that, if it becomes possible to identify cancer antigens that are specifically expressed on the surface of a cancer cell and to use antibodies targeting such antigens as medicaments, then treatment with antibody medicines that cause fewer side effects could be realized.

It has been reported that Mast Cell-Expressed Membrane Protein 1 (MCEMP1), a type 2 transmembrane protein, is expressed on cell membranes in a manner specific for mast cells, suggesting the possibility that the protein participates in mast cell differentiation, immune response, and allergic response (Non Patent Literature 1). However, none of the previous reports show that the MCEMP1 protein has immunity inducing activity against cancer cells and is thereby useful for treatment or prevention of cancers.

PRIOR ART LITERATURE

Non Patent Literature

Non Patent Literature 1: Kang Li. et al. Genomics, 86:68-75 (2005)

2

SUMMARY OF INVENTION

Technical Problem

An object of the present invention is to identify cancer antigen proteins specifically expressed on the surface of cancer cells and to provide a use of antibodies targeting such proteins as therapeutic and/or preventive agents for cancer.

Solution to Problem

As a result of intensive studies, the present inventors have now obtained cDNA encoding a protein that binds to an antibody present in the serum from a tumor-bearing organism by the SEREX method using canine testis tissue-derived cDNA libraries and sera from dogs with leukemia. With the use of the obtained canine genes and genes homologs from human, feline, and mouse, MCEMP1 proteins having amino acid sequences shown in SEQ ID NO: 2, 4, 6 or 8 and antibodies against the MCEMP1 proteins have now been prepared. In addition, the present inventors have now found that MCEMP1 is specifically expressed in the cells of leukemia, myelodysplastic syndrome, osteosarcoma, thymoma, mastocytoma, or perianal adenocarcinoma, and that portions of the MCEMP1 proteins are specifically expressed on the surface of such cancer cells. Further, the present inventors have now found that antibodies against the MCEMP1 portions expressed on cancer cell surfaces can damage cancer cells expressing MCEMP1. These findings have led to the completion of the present invention.

Therefore, the present invention includes aspects below.
(1) A pharmaceutical composition for treatment and/or prevention of a cancer, which comprises, as an active ingredient, an antibody or fragment thereof having an immunological reactivity with an MCEMP1 protein having the amino acid sequence shown in SEQ ID NO: 2, 4, 6, or 8 or an amino acid sequence having 80% or more sequence identity with the amino acid sequence, or with a fragment of the MCEMP1 protein comprising 7 or more consecutive amino acids.
(2) The pharmaceutical composition according to (1), which comprises, as an active ingredient, an antibody or fragment thereof having an immunological reactivity with a polypeptide comprising an extracellular region portion of the MCEMP1 protein, the polypeptide being a polypeptide consisting of 7 or more consecutive amino acids of the amino acid sequence shown in SEQ ID NO: 10, 12, 14, or 16, or a polypeptide consisting of an amino acid sequence having 80% or more sequence identity with the amino acid sequence.
(3) The pharmaceutical composition according to (1) or (2), wherein the cancer is a cancer expressing MCEMP1 on a cell surface.
(4) The pharmaceutical composition according to any one of (1) to (3), wherein the cancer is selected from the group consisting of leukemia, myelodysplastic syndrome, osteosarcoma, thymoma, mastocytoma, and perianal adenocarcinoma.
(5) The pharmaceutical composition according to any one of (1) to (4), wherein the antibody is a monoclonal or polyclonal antibody.
(6) The pharmaceutical composition according to any one of (1) to (5), wherein the antibody is a human antibody, a humanized antibody, a chimeric antibody, a single chain antibody, or a multispecific antibody.
(7) An antibody or fragment thereof having an immunological reactivity with a polypeptide comprising an extracellular region portion of an MCEMP1 protein, the polypeptide being a polypeptide consisting of the amino acid sequence shown in SEQ ID NO: 10, 12, 14, or 16 or an amino acid sequence having 80% or more sequence identity with the amino acid sequence.

(8) The antibody or fragment thereof according to (7), wherein the antibody is a human antibody, a humanized antibody, a chimeric antibody, a single chain antibody, or a multispecific antibody.

(9) A pharmaceutical combination for treatment and/or prevention of a cancer, which comprises the pharmaceutical composition according to any one of (1) to (6) and a pharmaceutical composition comprising an antitumor agent.

(10) A method for treating and/or preventing a cancer, which comprises administering, to a subject, an antibody or fragment thereof having an immunological reactivity with an MCEMP1 protein having the amino acid sequence shown in SEQ ID NO: 2, 4, 6, or 8 or an amino acid sequence having 80% or more sequence identity with the amino acid sequence, or with a fragment of the MCEMP1 protein comprising 7 or more consecutive amino acids.

This description includes all or part of the contents disclosed in Japanese Patent Application No. 2016-064035, to which the present application claims the priority.

Advantageous Effects of Invention

Antibodies against MCEMP1 used in the present invention damage cancer cells. Therefore, such antibodies against MCEMP1 are useful for treatment or prevention of cancers.

BRIEF DESCRIPTION OF DRAWINGS

FIG. 2A shows the expression patterns of the human MCEMP1 gene in each of human tissues. FIG. 2B shows the expression patterns of the human MCEMP1 gene in each of human cancer cell lines.

DESCRIPTION OF EMBODIMENTS

Figure 1:
FIG. 1 shows expression patterns of the identified canine MCEMP1 gene in canine tumor tissues.

The present invention relates to a use of an antibody or fragment (preferably antigen binding fragment) thereof to an MCEMP1 protein or a fragment thereof for treatment and/or prevention of cancers.

The present invention relates to a pharmaceutical composition for treatment and/or prevention of a cancer, which comprises, as an active ingredient, an antibody or fragment thereof having an immunological reactivity with an MCEMP1 protein having an amino acid sequence shown in SEQ ID NO: 2, 4, 6, or 8 or an amino acid sequence having 80% or more (preferably 85% or more, more preferably 90% or more, further preferably 95% or more, and particularly preferably 99% or more, for example, 99.5% or more) sequence identity with the amino acid sequence, or with a fragment of the MCEMP1 protein comprising 7 or more (7 to each full-length sequence, preferably 7 to 150 and more preferably 7 to 50) consecutive amino acids.

The present invention also relates to the pharmaceutical composition for treatment and/or prevention of a cancer, which comprises, as an active ingredient, an antibody or fragment thereof having an immunological reactivity with a partial polypeptide of the MCEMP1 protein, the partial polypeptide being a polypeptide consisting of 7 or more (7 to each full-length sequence, preferably 7 to 40, more preferably 7 to 20, for example, 7 to 12 or 8 to 11) consecutive amino acids of an amino acid sequence shown in any one of the even numbered SEQ ID NOS: 10 to 24, or a polypeptide consisting of an amino acid sequence having 80% or more (preferably 85% or more, more preferably 90% or more, further preferably 95% or more, and particularly preferably 97% or more) sequence identity with the amino acid sequence.

The antitumor activity of the antibody or fragment thereof to the polypeptide consisting of an amino acid sequence shown in SEQ ID NO: 2, 4, 6, or 8 or to a fragment of the polypeptide used in the present invention can be evaluated by examining in vivo the inhibition of tumor growth in a tumor-bearing animal, or, as described below, by examining in vitro whether or not immunocyte- or complement-mediated cytotoxic activity against tumor cells expressing the polypeptide is exhibited.

Likewise, the antitumor activity of the antibody or fragment thereof against the polypeptide consisting of an amino acid sequence shown in any one of the even numbered SEQ ID NOS: 10 to 16 or a fragment of the polypeptide used in the present invention can be evaluated by examining in vivo the inhibition of tumor growth in a tumor-bearing animal, or, as described below, by examining in vitro whether or not immunocyte- or complement-mediated cytotoxic activity against tumor cells expressing the polypeptide is exhibited.

In addition, the nucleotide sequences of polynucleotides encoding the proteins consisting of the amino acid sequences shown in SEQ ID NOS: 2, 4, 6, 8, 10, 12, 14, and 16 are shown in SEQ ID NOS: 1, 3, 5, 7, 9, 11, 13, and 15 respectively.

The amino acid sequence shown in SEQ ID NO: 4 in the Sequence Listing disclosed according to the present invention is the amino acid sequence of the MCEMP1, which was isolated, by the SEREX method using canine testis tissue-derived cDNA libraries and sera from dogs with leukemia, as a polypeptide capable of binding to antibodies specifically existing in the sera from tumor-bearing dogs; the amino acid sequence shown in SEQ ID NO: 2 is the amino acid sequence of the MCEMP1 isolated as a human homolog of said dog polypeptide; the amino acid sequence shown in SEQ ID NO: 6 is the amino acid sequence of the MCEMP1 isolated as a feline homolog of said dog polypeptide; and the amino acid sequence shown in SEQ ID NO: 8 is the amino acid sequence of the MCEMP1 protein isolated as a mouse homolog of said dog polypeptide (see Example 1 described below).

According to the present invention, an antibody that binds to a portion expressed on cancer cell surfaces within MCEMP1 protein is preferably used. Specific examples thereof include an amino acid sequence shown in SEQ ID NO: 10 (human), 12 (canine), 14 (feline), or 16 (mouse), which is a polypeptide comprising an extracellular region portion of the MCEMP1 protein, or fragments thereof (preferably, the fragments each consisting of 7 or more consecutive amino acids of any one of the amino acid sequences), or an amino acid sequence having 80% or more, preferably 85% or more, more preferably 90% or more, further preferably 95% or more, and particularly preferably 99% or more sequence identity to any one of these polypeptides. Antibodies of the present invention include all antibodies capable of binding to the above polypeptides and having antitumor activity.

The antibodies to MCEMP1 usable in the present invention as described above may be any types thereof, as long as they can exhibit antitumor activity. Examples thereof can include monoclonal antibodies, polyclonal antibodies, synthetic antibodies, multispecific antibodies (e.g., bispecific antibodies), human antibodies, humanized antibodies, chimeric antibodies, and single-chain antibodies (scFV). The antibodies used in the present invention also include antibody fragments, for example, antigen binding fragments such as Fab and F(ab')$_2$. These antibodies and fragments thereof can be prepared by methods known to persons skilled in the art. In the present invention, antibodies or fragments thereof capable of specifically binding to an MCEMP1 protein are desirable. Such antibodies are preferably monoclonal antibodies; however, as long as homogenous antibodies can be stably produced, polyclonal antibodies may also be used. In addition, if the subject is a human, a human antibody or a humanized antibody is desirable in order to avoid or inhibit the immunorejection.

The word "specifically binding to an MCEMP1 protein or fragments thereof" as used herein means that an antibody of interest specifically binds to the MCEMP1 protein or fragments thereof and does not substantially bind to other proteins.

The antitumor activity of an antibody used in the present invention can be evaluated by examining in vivo the inhibition of tumor growth in a tumor-bearing animal, or, as described below, examining in vitro whether or not the immunocyte- or complement-mediated cytotoxic activity against tumor cells expressing the polypeptide is exhibited.

Moreover, the subjects in need of treatment and/or prevention of cancer according to the present invention are mammals such as human, pet animals, livestock animals, sport animals, or experimental animals. The preferred subject is a human.

Production of antigens, production of antibodies, and pharmaceutical compositions, related to the present invention, will be explained below.

<Production of Antigens Used for Antibody Production>

Proteins or fragments thereof used as sensitizing antigens for obtaining antibodies to MCEMP1 used in the present invention are not limited in terms of their origins such as animals including, for example, humans, canines, felines, mice, bovines, horses, rats, and chickens. However, such proteins or fragments thereof are preferably selected in view of compatibility with parent cells used for cell fusion. Mammal-derived proteins are generally preferable and human-derived proteins are particularly preferable. For instance, if the MCEMP1 is human MCEMP1, a human MCEMP1 protein, a partial polypeptide thereof, or cells capable of expressing human MCEMP1 can be used.

Nucleotide sequences and amino acid sequences of human MCEMP1 and homologs thereof can be obtained by, for example, accessing the website of GenBank (NCBI, USA) and using an algorithm such as BLAST or FASTA (Karlin and Altschul, Proc. Natl. Acad. Sci. USA, 90:5873-5877, 1993; Altschul et al., Nucleic Acids Res. 25:3389-3402, 1997).

According to the present invention, when the nucleotide sequence (SEQ ID NO: 1) or the amino acid sequence (SEQ ID NO: 2) of human MCEMP1 is used as a base sequence, targets are nucleic acids or proteins each consisting of a sequence having 70% to 100%, preferably 80% to 100%, more preferably 90% to 100%, and further preferably 95% to 100% (e.g., 97% to 100%, 98% to 100%, 99% to 100%, or 99.5% to 100%) sequence identity with the nucleotide sequence or amino acid sequence of the ORF or mature portion of the base nucleotide sequence or amino acid sequence. The term "% sequence identity" as used herein means a percentage (%) of the number of identical amino acids (or nucleotides) to the total number of amino acids (or nucleotides) in the case that two sequences are aligned such that maximum similarity can be achieved with or without introduction of gaps.

Fragments of an MCEMP1 protein have lengths ranging from the amino acid length of an epitope (or an antigenic determinant), which is the smallest unit of an antigen recognized by an antibody, to less than the full-length of the protein. The epitope refers to a polypeptide fragment having antigenicity or immunogenicity in mammals and preferably in humans. The smallest unit of the epitope consists of approximately 7 to 12 amino acids, and for example, 8 to 11 amino acids. A specific example thereof is a polypeptide consisting of the amino acid sequence having 80% or more, preferably 85% or more, more preferably 90% or more, and further preferably 95% or more sequence identity with the amino acid sequence of an MCEMP1 protein.

Polypeptides comprising the aforementioned human MCEMP1 protein and partial peptides thereof can be synthesized according to chemical synthesis methods such as the Fmoc method (fluorenylmethyloxycarbonyl method) or the tBoc method (t-butyloxycarbonyl method) (the Japanese Biochemical Society (ed.), "Biochemical Experimentation Course (Seikagaku Jikken Koza) 1," Protein Chemistry IV, Chemical Modification and Peptide Synthesis, Kagaku-dojin Publishing Company, Inc. (Japan), 1981). Also, they can be synthesized by general methods using a variety of commercially available peptide synthesizers. In addition, polypeptides of interest can be obtained by preparing polynucleotides encoding the above polypeptides, incorporating each of the polynucleotides into an expression vector and introducing the vector into a host cell, thereby allowing the host cell to produce the polypeptide, using known gene engineering methods (Sambrook et al., Molecular Cloning, 2nd edition, Current Protocols in Molecular Biology (1989), Cold Spring Harbor Laboratory Press; Ausubel et al., Short Protocols in Molecular Biology, 3rd edition, A Compendium of Methods from Current Protocols in Molecular Biology (1995), John Wiley & Sons, etc.).

Polynucleotides encoding the aforementioned polypeptides can be readily prepared by known gene engineering techniques or general methods using commercially available nucleic acid synthesizers. For example, DNA comprising the nucleotide sequence shown in SEQ ID NO: 1 can be prepared by PCR using a human chromosome DNA or cDNA library as a template and a pair of primers designed to enable the amplification of the nucleotide sequence shown in SEQ ID NO: 1. PCR conditions can be appropriately determined. For example, such conditions may comprise conducting 30 cycles of the reaction steps (as one cycle)

consisting of: 94° C., 30 seconds (denaturation); 55° C., 30 seconds to 1 minute (annealing); and 72° C., 1 minute (elongation) using a thermostable DNA polymerase (e.g., Taq polymerase) and a $Mg^{2+}$-containing PCR buffer, followed by reaction at 72° C. for 7 minutes after completion of the 30 cycles. However, PCR conditions are not limited to the above-exemplified PCR conditions. PCR techniques and conditions are described in, for example, Ausubel et al., Short Protocols in Molecular Biology, 3rd edition, A Compendium of Methods from Current Protocols in Molecular Biology (1995), John Wiley & Sons (Chapter 15, in particular).

In addition, desired DNA can be isolated by preparing appropriate probes and primers based on information about the nucleotide and amino acid sequences shown in SEQ ID NOS: 1 to 8 in the Sequence Listing of the application, and screening a cDNA library of e.g. human with the use of such probes and primers. Preferably, such cDNA library is produced from a cell, organ, or tissue in which the protein with SEQ ID NO: 2, 4, 6 or 8 is expressed. Examples of the cell or tissue include, but not limited to, cells or tissues from cancers or tumors, such as bone marrow, peripheral blood mononuclear cell (PBMC), leukemia, myelodysplastic syndrome, osteosarcoma, thymoma, mastocytoma, and perianal adenocarcinoma. Operations such as preparation of probes or primers, construction of cDNA libraries, screening of cDNA libraries, and cloning of genes of interest, as described above, are known to persons skilled in the art, and they can be carried out according to, for example, the methods described in Sambrook et al., Molecular Cloning, the 2nd edition, Current Protocols in Molecular Biology (1989) and Ausubel et al. (ibid.). DNAs encoding human MCEMP1 protein and partial peptides thereof can be obtained from the thus obtained DNAs.

The above-described host cells may be any cells, as long as they can express the above-described polypeptides. An example of prokaryotic host cell includes, but is not limited to, *Escherichia coli*. Examples of eukaryotic host cells include, but are not limited to, mammalian cells such as monkey kidney cell (COS 1), Chinese hamster ovary cell (CHO), human embryonic kidney cell line (HEK293), and mouse embryonic skin cell line (NIH3T3), yeast cells such as budding yeast and fission yeast cells, silkworm cells, and *Xenopus laevis* egg cells.

When prokaryotic cells are used as host cells, an expression vector preferably having an origin replicable in prokaryotic cells, a promoter, a ribosome-binding site, a multicloning site, a terminator, a drug resistance gene, an auxotrophic complementary gene, a reporter gene, or the like can be used. As expression vectors for *Escherichia coli*, pUC vectors, pBluescriptII, pET expression systems, pGEX expression systems, and the like can be exemplified. A DNA encoding the above polypeptide is incorporated into such an expression vector, a prokaryotic host cell is transformed with the vector, and then the thus obtained transformed cell is cultured, so that the polypeptide encoded by the DNA can be expressed in the prokaryotic host cell. At this time, the polypeptide can also be expressed as a fusion protein with another protein.

When eukaryotic cells are used as host cells, expression vectors for eukaryotic cells preferably having a promoter, a splicing region, a poly(A) addition site, or the like can be used. Examples of such expression vectors include pKA1, pCDM8, pSVK3, pMSG, pSVL, pBK-CMV, pBK-RSV, EBV vector, pRS, pcDNA3.1, pSecTag (A, B, C) and pYES2. By similar procedures to those mentioned above, a DNA encoding the aforementioned polypeptide is incorporated into such an expression vector, an eukaryotic host cell is transformed with the vector, and then the thus obtained transformed cell is cultured, so that the polypeptide encoded by the above DNA can be expressed in the eukaryotic host cell. When pIND/V5-His, pFLAG-CMV-2, pEGFP-N1, pEGFP-C1, or the like is used as an expression vector, the above polypeptide may be expressed as a fusion protein with a tag, such as His tag (e.g., (His)6 to (His)10), FLAG tag, myc tag, HA tag, or GFP.

For introduction of an expression vector into a host cell, well known methods can be employed, such as electroporation, a calcium phosphate method, a liposome method, a DEAE dextran method, microinjection, viral infection, lipofection, and binding with a cell-membrane-permeable peptide.

Isolation and purification of a polypeptide of interest from host cells can be performed using known isolation techniques in combination. Examples of isolation and purification techniques include, but are not limited to, treatment using a denaturing agent such as urea or a surfactant, ultrasonication, enzymatic digestion, salting-out, solvent fractionation and precipitation, dialysis, centrifugation, ultrafiltration, gel filtration, SDS-PAGE, isoelectric focusing electrophoresis, ion exchange chromatography, hydrophobic chromatography, affinity chromatography, and reverse phase chromatography.

<Structure of Antibody>

In general, antibodies are heteromultimeric glycoproteins each comprising at least two heavy chains and two light chains. Meanwhile, another class of antibodies except for IgM are heterotetrameric glycoproteins (approximately 150 kDa) each comprising two identical light (L) chains and two identical heavy (H) chains. Typically, each light chain is connected to a heavy chain via a single covalent disulfide bond. However, the number of disulfide bonds between heavy chains varies among different immunoglobulin isotypes. Each of heavy chain and light chain also has an intrachain disulfide bond(s). Each heavy chain has a variable domain (VH region) at one end thereof, to which some constant regions are bound in series. Each light chain has a variable domain (VL region) at one end thereof and has a single constant region at the opposite end thereof. The constant region of a light chain is aligned with the first constant region of a heavy chain and the light-chain variable domain is aligned with the heavy-chain variable domain. A specific region of an antibody variable domain, which is called "complementarity determining region (CDR)," exhibits specific variability so as to impart binding specificity to an antibody. A relatively conserved portion in a variable region is called a "framework region (FR)." A complete heavy-chain or light-chain variable domain comprises 4 FRs connected to each other via 3 CDRs. Such CDRs are called "CDRH1," "CDRH2," and "CDRH3," respectively, in such order from the N-terminus in a heavy chain. Similarly, for a light chain, they are called "CDRL1," "CDRL2," and "CDRL3," respectively. CDRH3 plays the most important role in terms of antibody-antigen binding specificity. In addition, CDRs in each chain are retained by FR regions in the state that they are close to each other, and they contribute to the formation of antigen binding sites of an antibody together with CDRs in a corresponding chain. Constant regions do not directly contribute to antibody-antigen binding. However, they exhibit various effector functions such as association with antibody-dependent cytotoxicity (ADCC activity), phagocytosis through binding to an Fcγ receptor, half-life/clearance rate via a neonatal Fc receptor (FcRn), and complement-dependent cytotoxicity (CDC activity) via a C1q component in the complement cascade.

<Antibody Production>

The term "anti-MCEMP1 antibody" used in the present invention refers to an antibody having an immunological reactivity with a full-length MCEMP1 protein or a fragment thereof described above.

The term "immunological reactivity" used herein indicates the characteristics of an antibody binding in vivo or in vitro to an MCEMP1 antigen. The tumor- or tumor cell-damaging function (e.g., death, inhibition, or regression) can be expressed as a result of such binding. Specifically, any type of antibody may be used in the present invention as long as the antibody can bind to an MCEMP1 protein to damage a tumor, preferably a cancer expressing (or having) the MCEMP1 protein on a cell surface, such as leukemia, myelodysplastic syndrome, osteosarcoma, thymoma, mastocytoma, or perianal adenocarcinoma.

Examples of such antibodies include monoclonal antibodies, polyclonal antibodies, synthetic antibodies, multispecific antibodies (e.g., bispecific antibodies), human antibodies, humanized antibodies, chimeric antibodies, and single-chain antibodies. Examples of such antibodies also include antibody fragments (e.g., fragments such as Fab and $F(ab')_2$). In addition, antibodies may be any class of immunoglobulin molecules such as IgG, IgE, IgM, IgA, IgD, and IgY, or any subclass thereof such as IgG1, IgG2, IgG3, IgG4, IgA1, and IgA2.

Antibodies may be further modified via acetylation, formylation, amidation, phosphorylation, or pegylation (PEG), in addition to glycosylation.

Production examples for a variety of antibodies are described below.

The polyclonal antibodies that can be used in the present invention can be obtained in a manner described below.

Serum is obtained by immunizing small animals such as mice, human antibody-producing mice, or rabbits with a naturally occurring MCEMP1 protein, a recombinant MCEMP1 protein that has been expressed as a protein fused with GST or the like in a microorganism such as *Escherichia coli*, or a partial peptide thereof. The serum is purified via ammonium sulfate precipitation, protein A/protein G column chromatography, DEAE ion-exchange chromatography, affinity column chromatography with a column to which an MCEMP1 protein or a synthetic peptide is coupled, or the like for preparation of polyclonal antibodies. In the Examples described below, a mouse polyclonal antibody against a domain expressed on cancer cell surfaces in an MCEMP1 protein amino acid sequence was produced, and antitumor effects thereof were confirmed.

Other examples of the antibodies that can be used in the present invention include monoclonal antibodies. For example, monoclonal antibodies can be obtained in a manner described below. For example, cells expressing the MCEMP1 protein on their surfaces (such as a leukemia cell line U937 or the like) is administered to mice for immunization, followed by extraction of spleens from the mice. Cells are separated from each spleen and then are fused with mouse myeloma cells. Clones capable of producing an antibody having cancer cell growth inhibition action are selected from the obtained fusion cells (hybridomas). A monoclonal antibody-producing hybridoma having cancer cell growth inhibition action is isolated and cultured. An antibody of interest can be prepared via purification from the culture supernatant by a general affinity purification method.

Also, a monoclonal antibody-producing hybridoma can be produced in a manner described below, for example.

First, an animal is immunized with a sensitizing antigen by a known method. In a general method, immunization is carried out by intraperitoneally or subcutaneously injecting a sensitizing antigen into a mammal. Specifically, a sensitizing antigen is diluted with or suspended in PBS (Phosphate-Buffered Saline), physiological saline, or the like to an appropriate resultant amount. If desired, an appropriate amount of a conventional adjuvant (e.g., Freund's complete adjuvant) is mixed therewith. After emulsification takes place, the resultant is administered to a mammal several times every 4 to 21 days. In addition, an adequate carrier can be used for immunization with a sensitizing antigen.

As described above, after immunization of a mammal and confirmation of an increase to a desired antibody level in serum, immunocytes are collected from the mammal and subjected to cell fusion. Particularly preferable examples of immunocytes are splenocytes.

Mammalian myeloma cells are used as relevant parent cells subjected to fusion with the above immunocytes. For such myeloma cells, the following various examples of known cell lines are preferably used: P3U1 (P3-X63Ag8U1), P3 (P3×63Ag8.653) (J. Immunol. (1979) 123, 1548-1550), P3×63Ag8U.1 (Current Topics in Microbiology and Immunology (1978) 81, 1-7), NS-1 (Kohler. G. and Milstein, C. Eur. J. Immunol. (1976). 6, 511-519), MPC-11 (Margulies. D. H. et al., Cell (1976) 8, 405-415), SP2/0 (Shulman, M. et al., Nature (1978) 276, 269-270), FO (de St. Groth, S. F. et al., J. Immunol. Methods (1980) 35, 1-21), S194 (Trowbridge, I. S. J. Exp. Med. (1978) 148, 313-323), and R210 (Galfre, G. et al., Nature (1979) 277, 131-133).

Basically, cell fusion of immunocytes and myeloma cells described above can be carried out according to a known method such as the method of Kohler and Milstein et al. (Kohler, G. and Milstein, C. Methods Enzymol. (1981) 73, 3-46).

More specifically, cell fusion described above is carried out, for example, in the presence of a cell fusion promoter in a conventional nutrients-containing culture solution. Examples of a fusion promoter to be used include polyethylene glycol (PEG) and Sendai virus (HVJ: hemagglutinating virus of Japan). If desired, an adjuvant such as dimethylsulfoxide may be further added for improvement of fusion efficiency.

The proportion of immunocytes used to that of myeloma cells used can be arbitrarily determined. For example, the ratio of immunocytes to myeloma cells is preferably 1:1 to 10:1. Examples of a culture solution that can be used for cell fusion described above include an RPMI1640 culture solution and an MEM culture solution adequate for growth of the above myeloma cell lines as well as other conventional culture solutions used for this kind of cell culture. Further, a serum replacement such as fetal calf serum (FCS) can be used in combination therewith.

For cell fusion, the above immunocytes and myeloma cells are sufficiently mixed at predetermined amounts in the culture solution. A PEG solution (e.g., average molecular weight: approximately 1000 to 6000) that has been previously heated to approximately 37° C. is added thereto at a concentration of generally 30% to 60% (w/v), followed by mixing. This results in formation of hybridomas of interest. Subsequently, sequential addition of an appropriate culture solution and removal of the supernatant via centrifugation are repeatedly carried out to remove cell fusion agent(s) and the like that are not preferable for the growth of hybridomas.

The thus obtained hybridomas are cultured in a conventional selection culture solution such as an HAT culture solution (a culture solution comprising hypoxanthine, aminopterin, and thymidine) for selection. Culture in such an HAT culture solution is continuously carried out for a sufficient time period (generally several days to several weeks) for death of cells (non-fused cells) other than hybridomas of interest. Next, a conventional limiting dilution method is employed to screen for hybridomas producing antibodies of interest and to carry out single cloning.

Further, as well as obtaining the above hybridomas via immunization of non-human animals with antigens, it is also possible to obtain hybridomas that produce human antibodies having a desired activity (e.g., cell growth inhibition activity) by sensitizing human lymphocytes (e.g., human lymphocytes infected with EB virus) in vitro with a protein, protein-expressing cells, or a lysate thereof and fusing the sensitized lymphocytes with human-derived myeloma cells having the ability to permanently divide (e.g., U266) (accession no. TIB196).

Monoclonal antibody-producing hybridomas produced as above can be passaged in a conventional culture solution. In addition, they can be preserved in liquid nitrogen for a long period of time.

Specifically, immunization is carried out using a desired antigen or cells expressing a desired antigen as sensitizing antigen(s) according to a conventional immunization method. The obtained immunocytes are fused with known parent cells by a conventional cell fusion method. Then, monoclonal antibody-producing cells (hybridomas) are screened for by a conventional screening method. Thus, antibody production can be carried out.

A known human antibody-producing mouse used herein is, for example, a KM Mouse (Kirin Pharma/Medarex) or a XenoMouse (Amgen) (e.g., WO02/43478 and WO02/092812). When such mice are immunized with MCEMP1 proteins or fragments thereof, complete human polyclonal antibodies can be obtained from blood. In addition, complete human monoclonal antibodies can be produced by a method of fusing splenocytes collected from immunized mice with myeloma cells.

Antigen preparation can be carried out in accordance with a method such as a method using animal cells (JP Patent Publication (Kohyo) No. 2007-530068) or a method using a baculovirus (e.g., WO98/46777). If the immunogenicity of an antigen is low, an antigen is bound to a macromolecule having immunogenicity, such as albumin. Then, the antigen can be used for immunization.

Further, it is possible to use a gene recombinant antibody produced by cloning an antibody gene from a hybridoma, incorporating the clone into an adequate vector, introducing the vector into a host, and using a genetic engineering technique. (See, for example, Carl, A. K. Borrebaeck, James, W. Larrick, THERAPEUTIC MONOCLONAL ANTIBODIES, Published in the United Kingdom by MACMILLAN PUBLISHERS LTD, 1990.) Specifically, cDNA of a variable region (V region) of an antibody is synthesized from mRNA of a hybridoma with the use of a reverse transcriptase. After DNA encoding a V region of an antibody of interest is obtained, such DNA is ligated to desired DNA encoding an antibody constant region (C region). The resultant is incorporated into an expression vector. Alternatively, DNA encoding an antibody V region may be incorporated into an expression vector comprising DNA of an antibody C region. Such DNA is incorporated into an expression vector in a manner such that it is expressed under control of an expression control region such as an enhancer or a promoter. Next, host cells are transformed with such expression vector, thereby allowing the antibody to be expressed.

Monoclonal antibodies include human monoclonal antibodies and non-human animal monoclonal antibodies (e.g., mouse monoclonal antibodies, rat monoclonal antibodies, rabbit monoclonal antibodies, and chicken monoclonal antibodies). Monoclonal antibodies can be produced by culturing hybridomas obtained via fusion of myeloma cells and splenocytes from non-human mammals (e.g., mice or human antibody-producing mice) immunized with MCEMP1 proteins or fragments thereof.

A chimeric antibody is an antibody produced by combining sequences from different animals. An example thereof is an antibody consisting of mouse antibody heavy-chain and light-chain variable regions and human antibody heavy-chain and light-chain constant regions. Such a chimeric antibody can be produced by a known method. For example, a chimeric antibody can be obtained by ligating DNA encoding an antibody V region to DNA encoding a human antibody C region, incorporating the resultant into an expression vector, introducing the vector into a host, and allowing the host to produce an antibody.

Polyclonal antibodies include antibodies obtained by immunizing human antibody-producing animals (e.g., mice) with MCEMP1 proteins or fragments thereof.

A humanized antibody is an engineered antibody, and it is sometimes referred to as a "reshaped human antibody." A humanized antibody is constructed by transplanting CDRs of an immunized animal-derived antibody into complementarity determining regions of a human antibody. Also, general genetic engineering techniques therefor are known.

Specifically, a DNA sequence designed to ligate mouse antibody CDRs to framework regions (FRs) of a human antibody is synthesized by PCR method using several oligonucleotides prepared to have portions overlapping each other at their ends. A humanized antibody can be obtained by ligating the above obtained DNA to DNA encoding a human antibody constant region, incorporating the resultant into an expression vector, introducing the vector into a host, and allowing the host to produce an antibody production (see EP-A-239400 and WO96/02576). Human antibody FRs to be ligated to each other via CDRs are selected, provided that complementarity determining regions can form a good antigen binding site. If necessary, amino acids in framework regions of an antibody variable region may be substituted in such a manner that complementarity determining regions in a reshaped human antibody form an appropriate antigen binding site (Sato K. et al., Cancer Research 1993, 53: 851-856). In addition, the framework regions may be substituted with framework regions from various human antibodies (see WO99/51743).

After a chimeric antibody or a humanized antibody is produced, amino acids in a variable region (e.g., FR) or a constant region may be, for example, substituted with different amino acids.

Here, the amino acid substitution is a substitution of, for example, less than 15, less than 10, not more than 8, not more than 7, not more than 6, not more than 5, not more than 4, not more than 3, or not more than 2 amino acids, preferably 1 to 5 amino acids, and more preferably 1 or 2 amino acids. A substituted antibody should be functionally equivalent to an unsubstituted antibody. The substitution is preferably a conservative amino acid substitution, which is a substitution between amino acids having similar characteristics in terms of charge, side chains, polarity, aromaticity, and the like. For example, amino acids having similar characteristics can be classified into the following types: basic amino acids (arginine, lysine, and histidine); acidic amino acids (aspartic acid and glutamic acid); uncharged polar amino acids (glycine, asparagine, glutamine, serine, threonine, cysteine, and tyrosine); nonpolar amino acids (leucine, isoleucine, alanine, valine, proline, phenylalanine, tryptophan, and methionine); branched-chain amino acids (threonine, valine, isoleucine); and aromatic amino acids (phenylalanine, tyrosine, tryptophan, and histidine).

Antibodies of the present invention may be modified antibodies. An example of a modified antibody is an antibody bound to a molecule such as polyethylene glycol (PEG). Regarding modified antibody of the present invention, substances that bind to an antibody are not limited. Such a modified antibody can be obtained by chemically modifying an obtained antibody. A method of such modification has been already established in the field related to the present invention.

The expression "functionally equivalent" used herein indicates a situation in which an antibody of interest has biological or biochemical activity similar to that of an antibody of the present invention. Specifically, such antibody has a function of damaging tumors and causes essentially no rejection reaction when applied to humans. An example of such activity is cell growth inhibition activity or binding activity.

A known method for preparing a polypeptide functionally equivalent to a given polypeptide that is well known to persons skilled in the art is a method comprising introducing a mutation into a polypeptide. For instance, a person skilled in the art can adequately introduce a mutation into an antibody of the present invention using a site-specific mutagenesis method (Hashimoto-Gotoh, T. et al., (1995) Gene 152, 271-275; Zoller, M J., and Smith, M. (1983) Methods Enzymol. 100, 468-500; Kramer, W. et al., (1984) Nucleic Acids Res. 12, 9441-9456; Kramer, W. and Fritz, H J., (1987) Methods Enzymol. 154, 350-367; Kunkel, T A., (1985) Proc. Natl. Acad. Sci. USA. 82, 488-492; or Kunkel (1988) Methods Enzymol. 85, 2763-2766) or the like. Thus, an antibody functionally equivalent to the antibody of the present invention can be prepared.

An aforementioned antibody capable of recognizing an epitope of an MCEMP1 protein recognized by an anti-MCEMP1 antibody can be obtained by a method known to persons skilled in the art. For example, it can be obtained by: a method comprising determining an epitope of an MCEMP1 protein recognized by an anti-MCEMP1 antibody by a general method (e.g., epitope mapping) and producing an antibody using a polypeptide having an amino acid sequence contained in the epitope as an immunogen; or a method comprising determining an epitope of a produced antibody by a general method and selecting an antibody having an epitope identical to an epitope of an anti-MCEMP1 antibody. Here, the term "epitope" refers to a polypeptide fragment having antigenicity or immunogenicity in mammals and preferably in humans. The smallest unit thereof consists of approximately 7 to 12 amino acids and preferably 8 to 11 amino acids.

The affinity constant Ka (kon/koff) of an antibody of the present invention is preferably at least $10^7$ $M^{-1}$, at least $10^8$ $M^{-1}$, at least $5\times10^8$ $M^{-1}$, at least $10^9$ $M^{-1}$, at least $5\times10^9$ $M^{-1}$, at least $10^{10}$ $M^{-1}$, at least $5\times10^{10}$ $M^{-1}$, at least $10^{11}$ $M^{-1}$, at least $5\times10^{11}$ $M^{-1}$, at least $10^{12}$ $M^{-1}$, or at least $10^{13}$ $M^{-1}$.

An antibody of the present invention can be conjugated with an antitumor agent. Binding between an antibody and an antitumor agent can be carried out via a spacer having a group reactive to an amino group, a carboxyl group, a hydroxy group, a thiol group, or the like (e.g., an imidyl succinate group, a formyl group, a 2-pyridyldithio group, a maleimidyl group, an alkoxycarbonyl group, or a hydroxy group).

Examples of antitumor agents include the following antitumor agents known in references or the like: paclitaxel, doxorubicin, daunorubicin, cyclophosphamide, methotrexate, 5-fluorouracil, thiotepa, busulfan, improsulfan, piposulfan, benzodopa, carboquone, meturedopa, uredepa, altretamine, triethylenemelamine, triethylenephosphoramide, triethylenethiophosphoramide, trimethylolomelamine, bullatacin, bullatacinone, camptothecin, bryostatin, callystatin, cryptophycin 1, cryptophycin 8, dolastatin, duocarmycin, eleutherobin, pancratistatin, sarcodictyin, spongistatin, chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard, carmustine, chlorozotocin, fotemustine, lomustine, nimustine, ranimustine, calicheamicin, dynemicin, clodronate, esperamicin, aclacinomycin, actinomycin, authramycin, azaserine, bleomycin, cactinomycin, carabicin, carminomycin, carzinophilin, chromomycin, dactinomycin, detorubicin, 6-diazo-5-oxo-L-norleucine, ADRIAMYCIN, epirubicin, esorubicin, idarubicin, marcellomycin, mitomycin C, mycophenolic acid, nogalamycin, olivomycin, peplomycin, potfiromycin, puromycin, quelamycin, rodorubicin, streptonigrin, streptozocin, tubercidin, ubenimex, zinostatin, zorubicin, denopterin, pteropterin, trimetrexate, fludarabine, 6-mercaptopurine, thiamiprine, thioguanine, ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone, aminoglutethimide, mitotane, trilostane, frolinic acid, aceglatone, aldophosphamide glycoside, aminolevulinic acid, eniluracil, amsacrine, bestrabucil, bisantrene, edatraxate, defofamine, demecolcine, diaziquone, eflornithine, elliptinium acetate, epothilone, etoglucid, lentinan, lonidamine, maytansine, ansamitocine, mitoguazone, mitoxantrone, mopidanmol, nitraerine, pentostatin, phenamet, pirarubicin, losoxantrone, podophyllinic acid, 2-ethylhydrazide, procarbazine, razoxane, rhizoxin, schizophyllan, spirogermanium, tenuazonic acid, triaziquone, roridine A, anguidine, urethane, vindesine, dacarbazine, mannomustine, mitobronitol, mitolactol, pipobroman, gacytosine, docetaxel, chlorambucil, gemcitabine, 6-thioguanine, mercaptopurine, cisplatin, oxaliplatin, carboplatin, vinblastine, etoposide, ifosfamide, mitoxantrone, vincristine, vinorelbine, novantrone, teniposide, edatrexate, daunomycin, aminopterin, xeloda, ibandronate, irinotecan, topoisomerase inhibitor, difluoromethylornithine (DMFO), retinoic acid, capecitabine, and pharmacologically acceptable salts or derivatives thereof.

Alternatively, it is also possible to bind a radioactive isotope such as $^{211}$At, $^{131}$I, $^{125}$I, $^{90}$Y, $^{186}$Re, $^{188}$Re, $^{153}$Sm, $^{212}$Bi, $^{32}$P, $^{175}$Lu, or $^{176}$Lu known in references and the like to an antibody of the present invention. It is desirable for such radioactive isotopes to be effective for tumor treatment or diagnosis.

An antibody of the present invention is preferably an antibody having an immunological reactivity with MCEMP1 or an antibody capable of specifically recognizing MCEMP1. Such an antibody should be an antibody having a structure that allows a subject animal to which the antibody is administered to completely or almost completely avoid a rejection reaction. If the subject animal is a human, examples of such antibodies include human antibodies, humanized antibodies, chimeric antibodies (e.g., human-mouse chimeric antibodies), single-chain antibodies, and bispecific antibodies. Such an antibody is a recombinant antibody having human antibody-derived heavy-chain and light-chain variable regions, a recombinant antibody having heavy-chain and light-chain variable regions each consisting of non-human animal antibody-derived complementarity determining regions (CDR1, CDR2, and CDR3) and human antibody-derived framework regions, or a recombinant antibody having non-human animal antibody-derived heavy-chain and light-chain variable regions and human antibody-derived heavy-chain and light-chain constant regions. The first two antibodies are preferable.

The above recombinant antibody can be produced in the manner described below. DNA encoding a monoclonal antibody against human MCEMP1 (e.g., a human monoclonal antibody, a mouse monoclonal antibody, a rat monoclonal antibody, a rabbit monoclonal antibody, or a chicken monoclonal antibody) is cloned from an antibody-producing cell such as a hybridoma. DNAs encoding a light-chain variable region and a heavy-chain variable region of the antibody are produced by an RT-PCR method or the like using the obtained clone as a template. Then, the sequences of a light-chain variable region and a heavy-chain variable region or the sequences of CDR1, CDR2, and CDR3 are determined by the Kabat EU numbering system (Kabat et al., Sequences of Proteins of Immunological Interest, 5th Ed. Public Health Service, National Institute of Health, Bethesda, Md. (1991)).

Further, such DNAs encoding variable regions or DNAs encoding CDRs are produced by a genetic engineering technique (Sambrook et al., Molecular Cloning A Laboratory Manual, Cold Spring Harbor Laboratory Press (1989)) or a DNA synthesizer. Here, the above human monoclonal antibody-producing hybridoma can be produced by immunizing a human antibody-producing animal (e.g., a mouse) with human MCEMP1 and fusing splenocytes from the spleen removed from the animal with myeloma cells. In addition to the above, if necessary, DNAs encoding human antibody-derived light-chain or heavy-chain variable regions and constant regions are produced by a genetic engineering technique or a DNA synthesizer.

In the case of a humanized antibody, DNA in which the CDR coding sequences in a DNA encoding a human antibody-derived light-chain or heavy-chain variable region have been substituted with corresponding CDR coding sequences of an antibody from a non-human animal (e.g., a mouse, a rat, or a chicken) is produced. The DNA obtained as above is ligated to the DNA encoding a constant region of a human antibody-derived light chain or heavy chain. Thus, DNA encoding a humanized antibody can be produced.

In the case of a chimeric antibody, DNA encoding an antibody light-chain or heavy-chain variable region from a non-human animal (e.g., a mouse, a rat, or a chicken) is ligated to the DNA encoding a human antibody-derived light-chain or heavy-chain constant region. Thus, DNA encoding a chimeric antibody can be produced.

A single-chain antibody is an antibody in which a heavy-chain variable region and a light-chain variable region are linearly ligated to each other via a linker. DNA encoding a single-chain antibody can be produced by ligating DNA encoding a heavy-chain variable region, DNA encoding a linker, and a DNA encoding a light-chain variable region together. Here, a heavy-chain variable region and a light-chain variable region are those from a human antibody or those from a human antibody in which CDRs alone have been substituted with CDRs of an antibody from a non-human animal (e.g., a mouse, a rat, or a chicken). In addition, the linker consists of 12 to 19 amino acids. An example thereof is (G4S)3 consisting of 15 amino acids (G. B. Kim et al., Protein Engineering Design and Selection 2007, 20 (9): 425-432).

A bispecific antibody (diabody) is an antibody capable of specifically binding to two different epitopes. DNA encoding a bispecific antibody can be produced by, for example, ligating DNA encoding a heavy-chain variable region A, DNA encoding a light-chain variable region B, DNA encoding a heavy-chain variable region B, and DNA encoding a light-chain variable region A together in such order (provided that DNA encoding a light-chain variable region B and DNA encoding a heavy-chain variable region B are ligated to each other via DNA encoding a linker described above). Here, both a heavy-chain variable region and a light-chain variable region are those from a human antibody or those from a human antibody in which CDRs alone have been substituted with CDRs of an antibody from a non-human animal (e.g., a mouse, a rat, or a chicken).

Recombinant DNA produced as above is incorporated into one or a plurality of appropriate vector(s). Each such vector is introduced into a host cell (e.g., a mammal cell, a yeast cell, or an insect cell) for (co)expression. Thus, a recombinant antibody can be produced. See, P. J. Delves, ANTIBODY PRODUCTION ESSENTIAL TECH-NIQUES, 1997 WILEY, P. Shepherd and C. Dean, Monoclonal Antibodies, 2000 OXFORD UNIVERSITY PRESS; J. W. Goding, Monoclonal Antibodies: Principles and Practice, 1993 ACADEMIC PRESS.

The above antibodies preferably have cytotoxic activity, thereby exhibiting antitumor effects.

In addition, a hybridoma capable of producing a different human antibody or a non-human animal antibody (e.g., a mouse antibody) against human MCEMP1 is produced. A monoclonal antibody produced by the hybridoma is collected. Then, it is determined whether or not the obtained antibody is an antibody of interest using, as indicators, immunological binding activity to human MCEMP1 and cytotoxic activity. Thus, a monoclonal antibody-producing hybridoma of interest is identified. Thereafter, as described above, DNAs encoding heavy-chain and light-chain variable regions of an antibody of interest are produced from the hybridoma and sequenced. The DNAs are used for production of different antibodies.

Further, the above antibody of the present invention may be any one of antibodies having a substitution, deletion, or addition of one or several (and preferably, 1 or 2) amino acid(s), particularly in a framework region sequence and/or a constant region sequence, as long as it has the specific property of specifically recognizing MCEMP1. Here, the term "several amino acids" indicates 2 to 5 and preferably 2 or 3 amino acids.

Furthermore, according to the present invention, DNA encoding the above antibody of the present invention, DNA encoding a heavy chain or light chain of the antibody, or DNA encoding a heavy-chain or light-chain variable region of the antibody is also provided.

Complementarity determining regions (CDRs) encoded by DNAs of the above sequences are regions that determine antibody specificity. Therefore, sequences encoding the other regions (i.e., constant regions and framework regions) in an antibody may be sequences from a different antibody. Here, different antibodies include antibodies from non-human organisms. However, in view of reduction of side effects, human-derived antibodies are preferable. That is to say, in the above case, DNA regions encoding framework regions and constant regions of heavy and light chains preferably comprise nucleotide sequences encoding the relevant amino acid sequences from a human antibody.

DNA of the present invention can be obtained by, for example, the aforementioned methods or the following methods. First, total RNA is prepared from a hybridoma for an antibody of the present invention using a commercially available RNA extraction kit. Then, cDNA is synthesized with a reverse transcriptase using random primers and the like. Next, cDNA encoding an antibody is amplified by a PCR method using, as primers, oligonucleotides having sequences conserved in variable regions of known mouse antibody heavy-chain and light-chain genes. Sequences encoding constant regions can be obtained by amplifying known sequences by a PCR method. The nucleotide sequence of the DNA can be determined by a general method involving, for example, incorporation into a plasmid or phage for sequence determination.

It is thought that antitumor effects of an anti-MCEMP1 antibody used in the present invention upon MCEMP1-expressing cancer cells are exhibited through effector cell-mediated antibody-dependent cellular cytotoxicity (ADCC) activity against MCEMP1-expressing cells or complement-dependent cytotoxicity (CDC) activity against MCEMP1-expressing cells.

Accordingly, the activity of an anti-MCEMP1 antibody used in the present invention can be evaluated via in vitro determination of ADCC activity or CDC activity to MCEMP1-expressing cancer cells as specifically described in the Examples mentioned below.

An anti-MCEMP1 antibody used in the present invention binds to a MCEMP1-protein on a cancer cell and exhibits antitumor effects based on the above activity. Therefore, such antibody is believed to be useful for cancer treatment or prevention. Specifically, according to the present invention, a pharmaceutical composition for treatment and/or prevention of cancer that comprises, as an active ingredient, an anti-MCEMP1 antibody, is provided. When an anti-MCEMP1 antibody is used for the purpose of administering the antibody to humans (antibody treatment), it is preferably used in the form of a human antibody or a humanized antibody in order to reduce immunogenicity.

In addition, as the binding affinity between an anti-MCEMP1 antibody and an MCEMP1 protein on a cancer cell surface becomes higher, stronger antitumor activity can be exhibited by an anti-MCEMP1 antibody. Therefore, if an anti-MCEMP1 antibody having high binding affinity to an MCEMP1 protein can be obtained, even stronger antitumor effects can be expected to be exhibited. Accordingly, it becomes possible to use such antibody as a pharmaceutical composition for treatment and/or prevention of cancer. As described above, for high binding affinity, the affinity constant Ka (kon/koff) is preferably at least $10^7$ $M^{-1}$, at least $10^8$ $M^{-1}$, at least $5\times10^8$ $M^{-1}$, at least $10^9$ $M^{-1}$, at least $5\times10^9$ $M^{-1}$, at least $10^{10}$ $M^{-1}$, at least $5\times10^{10}$ $M^{-1}$, at least $10^{11}$ $M^{-1}$, at least $5\times10^{11}$ $M^{-1}$, at least $10^{12}$ $M^{-1}$, or at least $10^{13}$ $M^{-1}$.

<Binding to Antigen Expression Cells>

The capacity of an antibody to bind to MCEMP1 can be determined via binding assay using, for example, ELISA, a Western blot method, immunofluorescence, or flowcytometry analysis as described in the Examples.

<Immunohistochemical Staining>

An antibody that recognizes MCEMP1 can be tested in terms of reactivity with MCEMP1 by an immunohistochemical method well-known to persons skilled in the art using a frozen tissue section fixed with paraformaldehyde or acetone or a paraffin-embedded tissue section fixed with paraformaldehyde. Such section is prepared from a tissue obtained from a patient during surgery, a bone marrow tissue, lymph node, or peripheral blood cells of a patient, or a tissue obtained from an animal carrying xenograft tissue that has been inoculated with a cell line that expresses MCEMP1 naturally or after transfection thereof.

For immunohistochemical staining, an antibody immunologically reactive to MCEMP1 can be stained by a variety of methods. For example, it can be visualized by reacting with a horseradish peroxidase-conjugated goat anti-mouse antibody or goat anti-rabbit antibody.

<Pharmaceutical Composition>

The present invention provides a pharmaceutical composition (or medicament) comprising an antibody of the present invention, i.e., an antibody against MCEMP1 or fragment (preferably antigen binding fragment) thereof described above. The pharmaceutical composition (or medicament) of the present invention usually comprises an effective amount of the antibody against MCEMP1 or fragment (preferably antigen binding fragment) thereof described above.

A target of the pharmaceutical composition for treatment and/or prevention of a cancer of the present invention is not particularly limited as long as the target is a cancer (cell) expressing the MCEMP1 gene.

Both the terms "tumor" and "cancer" used herein refer to malignant neoplasm, and thus they are used in an exchangeable manner.

A cancer that can be a target in the present invention is a cancer expressing a gene encoding a polypeptide comprising an amino acid sequence of SEQ ID NO: 2, 4, 6, or 8 or a partial sequence consisting of 7 or more consecutive amino acids of said amino acid sequence, and is preferably a cancer expressing such a polypeptide on a cell surface. The cancer that can be a target in the present invention is preferably leukemia, myelodysplastic syndrome, osteosarcoma, thymoma, mastocytoma, or perianal adenocarcinoma. Examples of these specific cancers include, but are not limited to, acute non-lymphocytic leukemia, chronic lymphocytic leukemia, acute granulocytic leukemia, chronic granulocytic leukemia, acute promyelocytic leukemia, adult T-cell leukemia, aleukemic leukemia, leukocythemic leukemia, basophilic leukemia, blastic leukemia, bovine leukemia, chronic myeloleukemia, leukemia cutis, embryonal leukemia, eosinophilic leukemia, Gross leukemia, Rieder cell leukemia, Schilling's leukemia, stem cell leukemia, subleukemic leukemia, undifferentiated cell leukemia, hairy cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphotropic leukemia, lymphoid leukemia, lymphosarcoma cell leukemia, mast cell leukemia, megakaryocytic leukemia, micromyeloblastic leukemia, monocytic leukemia, myeloblastic leukemia, myeloleukemia, myeloid granulocytic leukemia, myelomonocytic leukemia, Naegeli leukemia, plasma cell leukemia, plasmacytic leukemia, promyelocytic leukemia, refractory anemia (RA), refractory anemia with ringed sideroblasts (RARS), refractory anemia with excess blasts (RAEB), RAEB in transformation (RAEB-T), preleukemia and chronic myelomonocytic leukemia (CMML), conventional central osteosarcoma and subtypes of osteosarcoma (intraosseous well-differentiated osteosarcoma, round cell osteosarcoma, surface osteosarcoma, periosteal osteosarcoma, periosteal osteosarcoma and high-grade surface osteosarcoma), thymoma, mastocytoma, perianal adenoma, and perianal adenocarcinoma.

In addition, the subject animal of the present invention is a mammal. Examples thereof include mammals such as primates, pet animals, livestock animals, sport animals, and experimental animals. Humans, dogs, and cats are particularly preferable.

When an antibody used in the present invention is used as a pharmaceutical composition, it can be formulated by a method known to persons skilled in the art. For instance, it can be parenterally used in the form of a parenteral injection of: an aseptic solution comprising water or a pharmacologically acceptable non-water solution; or a suspension liquid. For example, in one possible case, it can be formulated with the combined use of a pharmacologically acceptable carrier or medium or additive and specifically sterilized water, physiological saline, plant oil, an emulsifier, a suspension, a surfactant, a stabilizer, a flavoring agent, an excipient, a vehicle, a preservative, or a binder in an appropriate manner by mixing in a unit dosage form required for a generally acceptable pharmaceutical formulation. The amount of an active ingredient in a formulation is determined such that an appropriate dosage within the indicated range can be achieved.

An aseptic composition for injection purposes can be formulated in accordance with general formulation practice using a vehicle such as distilled water for injection purposes.

Examples of an aqueous solution for injection purposes include physiological saline and isotonic solutions comprising glucose and other adjuvants such as D-sorbitol, D-mannose, D-mannitol, and sodium chloride. Such solution may be used with an appropriate dissolution aid. Examples of such dissolution aid include alcohols such as ethanol and polyalcohol, propylene glycol, polyethylene glycol, and nonion surfactants such as polysorbate 80™ and HCO-60.

Examples of oily liquid include sesame oil and soybean oil. Such oily liquid may be used in combination with a dissolution aid such as benzyl benzoate or benzyl alcohol. In addition, it may be mixed with a buffering agent such as a phosphate buffer solution, a sodium acetate buffer solution, a soothing agent such as procaine hydrochloride, a stabilizer such as benzyl alcohol, phenol, or an antioxidant. In general, a formulated injection solution is introduced into an adequate ample.

The above pharmaceutical composition is orally or parenterally administered. Preferably, it is parenterally administered. Specific examples of dosage forms include injectable dosage form, intranasally-administered dosage form, transpulmonarily-administered dosage form, and percutaneously-administered dosage form. For example, injectable dosage form can be systemically or locally administered via intravenous injection, intramuscular injection, intraperitoneal injection, or subcutaneous injection. Alternatively, an antibody of the present invention may be administered directly to a tumor by local administration, such as injection, infusion, or implantation of a sustained-release formation, to the tumor.

In addition, the administration method can be appropriately determined depending on patient age, weight, gender, and symptoms. A single dose of a pharmaceutical composition comprising an antibody or a polynucleotide encoding an antibody can be selected within a range of, for example, 0.0001 mg to 1000 mg per kg of body weight. Alternatively, the dose can be selected within a range of, for example, 0.001 to 100000 mg per patient's body; however, it is not necessarily limited thereto. The dose and the administration method are changed depending on patient age, weight, gender, and symptoms. However, persons skilled in the art can appropriately select the dose and the method.

The cancer described above, particularly, a cancer expressing MCEMP1 on a cell surface, preferably leukemia, myelodysplastic syndrome, osteosarcoma, thymoma, mastocytoma, or perianal adenocarcinoma can be treated and/or prevented by administering an antibody of the present invention or fragment thereof, or the pharmaceutical composition comprising the same to a subject.

Further, a method for treating and/or preventing a cancer, which comprises administering, to a subject, the pharmaceutical composition (or medicament) of the present invention in combination with an antitumor agent as listed above or a pharmaceutical composition (or medicament) comprising the antitumor agent, is also included in the present invention. A target cancer is the same as above. The antibody or fragment thereof according to the present invention and the antitumor agent can be administered concurrently or separately to the subject. In the case of separately administering them, either of the pharmaceutical compositions can be administered first or later, and their dosing intervals, doses, administration routes, and the number of doses can be appropriately selected by a specialist physician. In the case of concurrently administering them, for example, a pharmaceutical composition in a dosage form obtained by mixing the antibody or fragment thereof according to the present invention and the antitumor agent in a pharmacologically acceptable carrier (or medium) for formulation is also included in the present invention. The description about prescription, formulation, administration routes, doses, cancers, etc. regarding pharmaceutical compositions and dosage forms containing antibodies of the present invention is applicable to all of the pharmaceutical compositions and dosage forms containing antitumor agents.

Accordingly, the present invention also provides a pharmaceutical combination for treatment and/or prevention of a cancer, which comprises the pharmaceutical composition of the present invention and a pharmaceutical composition comprising an antitumor agent as listed above, and a method for treating and/or preventing a cancer, which comprises administering the same. In addition, the present invention also provides a pharmaceutical composition for treatment and/or prevention of a cancer, which comprises an antibody of the present invention or fragment thereof and an antitumor agent together with a pharmacologically acceptable carrier and/or additive.

EXAMPLES

The present invention is hereafter described in greater detail with reference to the following examples, although the scope of the present invention is not limited thereto.

Example 1: Identification of New Cancer Antigen Protein by SEREX Method (1) Construction of cDNA Library Total RNA was extracted from a testis tissue of a healthy dog by an Acid guanidium-Phenol-Chloroform method and then a polyA RNA was purified according to protocols included with an Oligotex-dT30 mRNA purification Kit (Takara Shuzo Co., Ltd.).

A canine testis cDNA phage library was synthesized using the thus obtained mRNA (5 μg). The cDNA phage library was constructed using a cDNA Synthesis Kit, a ZAP-cDNA Synthesis Kit, and a ZAP-cDNA GigapackIII Gold Cloning Kit (STRATAGENE) according to protocols included with the kits. The size of the thus constructed cDNA phage library was 1×10⁶ pfu/ml.

(2) Screening of cDNA Library Using Serum

Immunoscreening was performed using the above con- structed canine testis cDNA phage library. Specifically, host *Escherichia coli* (XL1-Blue MRF) was infected with the phage on an NZY agarose plate (Φ90×15 mm) so as to obtain approximately 2500 clones. *E. coli* cells were cul- tured at 42° C. for 3 to 4 hours to form plaques. The plate was covered with a nitrocellulose membrane (Hybond C Extra: GE Healthcare Bio-Science) impregnated with IPTG (isopropyl-β-D-thiogalactoside) at 37° C. for 4 hours, so that the protein was induced, expressed, and then transferred to the membrane. Subsequently, the membrane was taken and then immersed in TBS (10 mM Tris-HCl, 150 mM NaCl, and pH 7.5) containing 0.5% powdered skim milk, followed by overnight shaking at 4° C., thereby suppressing nonspe- cific reaction. The filter was reacted with a 500-fold diluted serum of a canine patient at room temperature for 2 to 3 hours.

As the above serum of a canine patient, a serum collected from a canine patient with leukemia was used. These sera were stored at −80° C. and then subjected to pre-treatment immediately before use. A method for pretreatment of serum is as follows. Specifically, host *Escherichia coli* (XL1-Blue MRF') was infected with a λ ZAP Express phage in which no foreign gene had been inserted and then cultured over- night on a NZY plate medium at 37° C. Subsequently, buffer (0.2 M NaHCO₃ and pH 8.3) containing 0.5 M NaCl was added to the plate, the plate was left to stand at 4° C. for 15 hours, and then a supernatant was collected as an *Escheri- chia coli*/phage extract. Next, the thus collected *Escherichia coli*/phage extract was applied to an NHS-column (GE Healthcare Bio-Science), so that an *Escherichia coli*-phage- derived protein was immobilized. The serum of a canine patient was applied to the protein-immobilized column for reaction and then an antibody adsorbed to the *Escherichia coli* and phage were removed from the serum. The serum fraction that had passed through the column was diluted 500-fold with TBS containing 0.5% powdered skim milk. The resultant was used as an immunoscreening material.

The above membrane onto which the treated serum and the protein had been blotted was washed 4 times with TBS-T (0.05% Tween20/TBS) and then caused to react with goat anti-dog IgG (Goat anti-Dog IgG-h+L HRP conjugated (BETHYL Laboratories)) diluted 5000-fold with TBS con- taining 0.5% powdered skim milk as a secondary antibody for 1 hour at room temperature. Detection was performed via an enzyme coloring reaction using an NBT/BCIP reaction solution (Roche). Colonies that matched sites positive for a coloring reaction were collected from the NZY agarose plate ((D90×15 mm) and then lysed in 500 μl of an SM buffer (100 mM NaCl, 10 mM MgClSO₄, 50 mM Tris-HCl, 0.01% gelatin, and pH 7.5). Until colonies positive for coloring reaction were unified, secondary screening and tertiary screening were repeated so that approximately 10,000 phage clones reacting with serum IgG were screened for by a method similar to the above. Thus, 1 positive clone was isolated.

(3) Homology Search for Isolated Antigen Gene

For nucleotide sequence analysis of the 1 positive clone isolated by the above method, a procedure for conversion from phage vectors to plasmid vectors was performed. Specifically, 200 μl of a solution was prepared to contain host *Escherichia coli* (XL1-Blue MRF') so that absorbance OD₆₀₀ was 1.0. The solution was mixed with 100 μl of a purified phage solution and then with 1 μl of an ExAssist helper phage (STRATAGENE), followed by 15 minutes of reaction at 37° C. Three (3) ml of LB medium was added and then culture was performed at 37° C. for 2.5 to 3 hours. Immediately after culture, the temperature of the solution was kept at 70° C. by water bath for 20 minutes, centrifu- gation was performed at 4° C. and 1000×g for 15 minutes, and then the supernatant was collected as a phagemid solution. Subsequently, 200 μl of a solution was prepared to contain phagemid host *Escherichia coli* (SOLR) so that absorbance OD₆₀₀ was 1.0. The solution was mixed with 10 μl of a purified phage solution, followed by 15 minutes of reaction at 37° C. The solution (50 μl) was seeded on LB agar medium containing ampicillin (final concentration of 50 μg/ml) and then cultured overnight at 37° C. Transformed SOLR single colony was collected and then cultured in LB medium containing ampicillin (final concentration: 50 μg/ml) at 37° C. A plasmid DNA containing the insert of interest was purified using a QIAGEN plasmid Miniprep Kit (QIAGEN).

The purified plasmid was subjected to analysis of the full-length insert sequence by a primer walking method using the T3 primer of SEQ ID NO: 17 and the T7 primer of SEQ ID NO: 18. As a result of sequence analysis, the gene sequence of SEQ ID NO: 3 was obtained. A sequence identity search program, BLAST search (http:// www.ncbi.nlm.nih.gov/BLAST/), was performed using the nucleotide sequence of the genes and the amino acid sequence thereof. As a result of this sequence identity search with known genes, it was revealed that the obtained gene was MCEMP1 gene. The sequence identity with human MCEMP1, a human homolog of canine MCEMP1, was 70% in terms of nucleotide sequence and 51% in terms of amino acid sequence. The sequence identity with feline MCEMP1 was 83% in terms of nucleotide sequence and 64% in terms of amino acid sequence. The sequence identity with mouse MCEMP1, a mouse homolog of canine MCEMP1, was 65% in terms of nucleotide sequence and 47% in terms of amino acid sequence. The nucleotide sequence of human MCEMP1 is shown in SEQ ID NO: 1 and the amino acid sequence of the same is shown in SEQ ID NO: 2. The nucleotide sequence of feline MCEMP1 is shown in SEQ ID NO: 5 and the amino acid sequence of the same is shown in SEQ ID NO: 6. The nucleotide sequence of mouse MCEMP1 is shown in SEQ ID NO: 7 and the amino acid sequence of the same is shown in SEQ ID NO: 8.

(4) Gene Expression Analysis in Each Tissue

Figure 2:
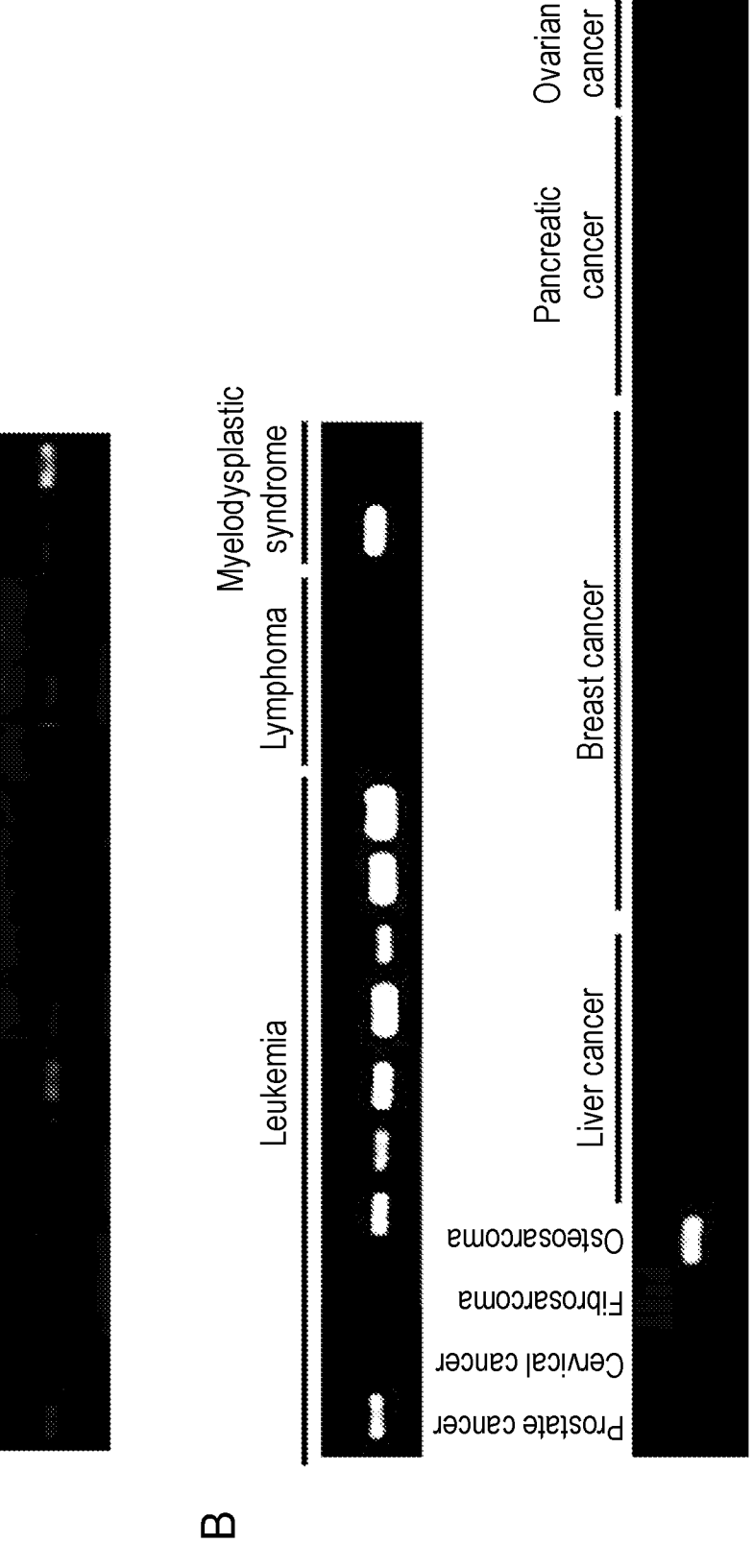
FIG. 2 shows expression patterns of the identified MCEMP1 gene in each of human tissues and cancer cell lines.
Figure 3:
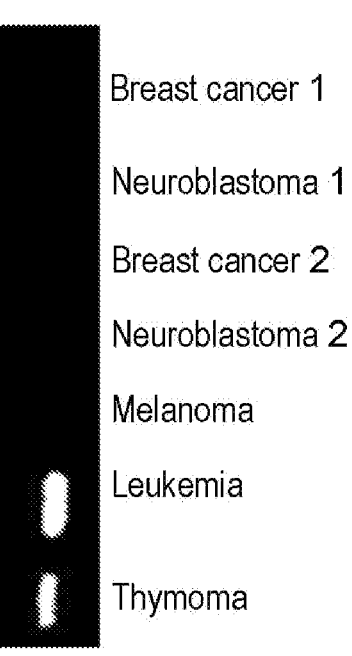
FIG. 3 shows expression patterns of the identified mouse MCEMP1 gene in each of mouse cancer cell lines.

Expression of the gene obtained by the above method in canine, human, and mouse various normal tissues, various tumor tissues, and various cancer cell lines was examined by an RT-PCR (reverse transcription-PCR) method. A reverse transcription reaction was performed as follows. Specifi- cally, total RNA was extracted from each tissue (50 mg to 100 mg) and each cell line (5 to 10×10⁶ cells) using a TRIZOL reagent (Thermo Fisher Scientific) according to protocols included therewith. cDNA was synthesized using the total RNA and Superscript First-Strand Synthesis Sys- tem for RT-PCR (Thermo Fisher Scientific) according to protocols included with the kit. Gene Pool cDNA (Thermo Fisher Scientific), QUICK-Clone cDNA (Clontech Labora- tories, Inc.), and Large-Insert cDNA Library (Clontech Laboratories, Inc.) were used as cDNAs from human normal tissues (brain, testis, colon, and placenta). PCR was per- formed as follows using primers specific to the obtained gene (canine primers: SEQ ID NOS: 19 and 20, human primers: SEQ ID NOS: 21 and 22, mouse primers: SEQ ID NOS: 23 and 24). Specifically, PCR was performed by repeating 30 times a cycle of 94° C./30 seconds, 55° C./30 seconds, and 72° C./1 minute using a Thermal Cycler (BIO RAD) and a reaction solution adjusted to a total amount of 25 μl through addition of each reagent and an attached buffer (0.25 μl of the cDNA sample prepared by reverse transcription reaction, the above primers (2 μM each), dNTP (0.2 mM each), and 0.65 U of ExTaq polymerase (Takara Shuzo)). As a result, as shown in FIG. 1, strong expression of the canine MCEMP1 gene was observed in mastocytoma and perianal adenocarcinoma in the case of canine tumor tissues (FIG. 1). Furthermore, expression of the human MCEMP1 gene was not observed in almost all healthy human tissues. On the other hand, strong expression of the human MCEMP1 gene was observed in the cell lines of leukemia, myelodysplastic syndrome, and osteosarcoma, in the case of human cancer cells (FIG. 2). Furthermore, expression of the mouse MCEMP1 gene was detected in the cell lines of leukemia, melanoma, and neuroblastoma (FIG. 3).

Example: 2 Preparation of Human MCEMP1 Protein (1) Cloning of Full-Length cDNA Encoding Human MCEMP1, and cDNA Encoding Extracellular Region of Human MCEMP1

Full-length cDNA encoding human MCEMP1 was cloned by the following method based on the gene of SEQ ID NO: 1 obtained in Example 1. PCR was performed by repeating 30 times a cycle of 98° C./10 seconds, 55° C./15 seconds, and 72° C./1 minute using a Thermal Cycler (BIO RAD) and a reaction solution adjusted to a total amount of 50 μl through addition of each reagent and an attached buffer (1 μl of cDNA (which was from a variety of tissue/cell-derived cDNAs prepared in Example 1 and observed for their expression by RT-PCR), 2 types of primers (0.4 μM each; SEQ ID NOS: 25 and 26) containing EcoRI and NotI restriction enzyme cleavage sequences, 0.2 mM dNTP, 1.25 U PrimeSTAR HS polymerase (Takara Shuzo)). The above 2 types of primers were used to amplify the region encoding the full-length amino acid sequence of SEQ ID NO: 2. After PCR, the thus amplified DNA was subjected to 1% agarose gel electrophoresis and then a DNA fragment of approximately 0.6 kbp was purified using a QIAquick Gel Extraction Kit (QIAGEN). The thus obtained PCR amplification product was inserted into pcDNA3.1 (Thermo Fisher Scientific) (hereinafter, the resultant is referred to as human MCEMP1/pcDNA3.1). The amplification product was also confirmed, by sequencing using a DNA sequencer, to have a cDNA sequence encoding human MCEMP1. The sequence shown in SEQ ID NO: 1 is the nucleotide sequence of the human MCEMP1 gene, and the sequence shown in SEQ ID NO: 2 is the amino acid sequence of the human MCEMP1 protein.

Further, PCR was performed based on SEQ ID NO: 1 by repeating 30 times a cycle of 98° C./10 seconds, 55° C./15 seconds, and 72° C./30 seconds using a Thermal Cycler (BIO RAD) and a reaction solution adjusted to a total amount of 50 μl through addition of each reagent and an attached buffer (2 types of primers (0.4 μM each; SEQ ID NOS: 27 and 28) containing KpnI and EcoRI restriction enzyme cleavage sequences, 0.2 mM dNTP, 1.25 U PrimeSTAR HS polymerase (Takara Shuzo)). The above 2 types of primers were used to amplify the region encoding SEQ ID NO: 10 comprising the amino acid sequence of the extracellular region of the MCEMP1 protein, in SEQ ID NO: 1. After PCR, the thus amplified DNA was subjected to 1% agarose gel electrophoresis and then a DNA fragment of approximately 0.3 kbp was purified using a QIAquick Gel Extraction Kit (QIAGEN). The thus obtained PCR amplification product was ligated to pSecTagB (Thermo Fisher Scientific) having an insert of cDNA encoding the mouse IgG2a Fc protein to prepare an expression vector encoding a human MCEMP1 extracellular region/mouse IgG2a Fc fusion protein (hereinafter, referred to as hMCEMP1 ECD-mIgG2 aFc) (hereinafter, the obtained expression vector is referred to as pSecB-hMCEMP1 ECD-mIgG2 aFc). The amplification product was also confirmed, by sequencing using a DNA sequencer, to have a cDNA sequence encoding hMCEMP1 ECD-mIgG2 aFc. The sequence shown in SEQ ID NO: 29 is the nucleotide sequence encoding hMCEMP1 ECD-mIgG2 aFc, and the sequence shown in SEQ ID NO: 30 is the amino acid sequence of hMCEMP1 ECD-mIgG2 aFc.

(2) Preparation of hMCEMP1 ECD-mIgG2 aFc hMCEMP1 ECD-mIgG2 aFc was prepared as an immunizing antigen for preparing antibodies to MCEMP1.

The expression vector pSecB-hMCEMP1 ECD-mIgG2 aFc was introduced by the lipofection method into human embryonic kidney cell line HEK293 cells and purification of hMCEMP1 ECD-mIgG2 aFc was carried out from a culture supernatant obtained 7 days after introduction. The culture supernatant was applied to a Hi Trap Protein A HP column (GE Healthcare Bio-Science), which was then washed with a binding buffer (20 mM sodium phosphate (pH 7.0)), followed by elution with an elution buffer (0.1 M glycine-HCl (pH 2.7)). Eluates were immediately neutralized by elution into a tube supplemented with a neutralization buffer (1 M Tris-HCl (pH 9.0)). Next, the buffer in the eluates obtained by the above method was replaced with physiological phosphate buffer (Nissui Pharmaceutical Co., Ltd.) using ultrafiltration NANOSEP 10K OMEGA (PALL). Sterilized filtration was performed using 0.22-μm HT Tuffryn Acrodisc (PALL) and then the resultants were used for the following experiments.

Example 3: Preparation of Polyclonal Antibody Binding to Extracellular Region of MCEMP1

(1) Preparation of Polyclonal Antibody to MCEMP1

To obtain an antibody binding to the extracellular region of MCEMP1, hMCEMP1 ECD-mIgG2 aFc (0.1 mg) prepared as described above as an antigen was mixed with a complete Freund's adjuvant (CFA) solution in an amount equivalent thereto. The mixture was subcutaneously administered to a mouse 4 times every 2 weeks. Subsequently, blood was collected, so that an antiserum containing a polyclonal antibody was obtained. Furthermore, the antiserum was purified using a protein G carrier (GE Healthcare Bio-Sciences) and then a polyclonal antibody against hMCEMP1 ECD-mIgG2 aFc was obtained. In addition, an antibody obtained by purifying serum of mice to which no antigen had been administered with the use of a protein G carrier in the manner described above was designated as a control antibody.

(2) Establishment of Cells Stably Expressing Full-Length Human MCEMP1

Human MCEMP1/pcDNA3.1 prepared as described above was introduced by the lipofection method into CHO-K1 cells (ATCC) and then selection was performed using 500 μg/ml G418 (Nacalai Tesque, Inc.) to establish a CHO cell line stably expressing full-length human MCEMP1 (CHO-human MCEMP1). Cells obtained by introducing an expression vector (hereinafter, referred to as emp/pcDNA3.1) having no insert of cDNA encoding MCEMP1 and then performing selection in the manner described above was designated as control cells (hereinafter, referred to as CHO-emp).

(3) Analysis of Antigen Protein Expression on Cell Surface

Next, it was examined whether or not the polyclonal antibody prepared in (1) above specifically reacted with MCEMP1 expressed on the surfaces of the cells established in (2) above. The CHO-human MCEMP1 cells or the CHO-emp cells ($10^6$ cells each) were centrifuged in a 1.5-ml microcentrifugal tube. The polyclonal antibody against MCEMP1 (2 µg) (5 µl) prepared in (1) above was added thereto. The resultant was further suspended in PBS containing 0.1% fetal bovine serum (95 µl) and then left to stand on ice for 1 hour. After washing with PBS, the resultant was suspended in PBS containing an FITC-labeled goat anti-mouse IgG antibody (Santa Cruz Biotechnology, Inc.) (5 µl) and 0.1% fetal bovine serum (FBS) (95 µl) and then left to stand on ice for 1 hour. After washing with PBS, fluorescence intensity was measured using FACSCalibur (Becton, Dickinson and Company). Meanwhile, a procedure similar to the above was performed using the control antibody prepared in (1) above instead of the polyclonal antibody against MCEMP1, so that a control was prepared. As a result, 208% increase in fluorescence intensity was found in the CHO-human MCEMP1 cells to which the anti-human MCEMP1 antibody had been added, as compared with the control. Meanwhile, a procedure similar to the above was performed for the CHO-emp cells. As a result, 0% increase in fluorescence intensity was found in the CHO-emp cells to which the anti-human MCEMP1 antibody had been added, as compared with the control. Based on the above, it was revealed that the anti-human MCEMP1 antibody was capable of specifically binding to the MCEMP1 protein expressed on the cell membrane surfaces. In addition, the rate of increase in fluorescence intensity is represented by the rate of increase in mean fluorescence intensity (MFI value) in cells. It was calculated by the following equation.

Rate of increase in mean fluorescence intensity (rate of increase in fluorescence intensity)(%)=((MFI value of cells reacted with an anti-human MCEMP1 antibody)–(control MFI value))/(control MFI value)×100

Next, it was examined whether or not the MCEMP1 protein was expressed on cell surfaces of 2 types of leukemia cell lines (U937 and THP-1) and 1 type of myelodysplastic syndrome cell line (MDS92) in which MCEMP1 gene expression had been strongly confirmed. Each human cell line ($10^6$ cells) in which gene expression had been confirmed as described above was centrifuged in a 1.5-ml microcentrifugal tube. The polyclonal antibody against MCEMP1 (2 µg) (5 µl) prepared in (1) above was added thereto. The resultant was further suspended in PBS containing 0.1% fetal bovine serum (95 µl) and then left to stand on ice for 1 hour. After washing with PBS, the resultant was suspended in PBS containing an FITC-labeled goat anti-mouse IgG antibody (Santa Cruz Biotechnology, Inc.) (5 µl) and 0.1% fetal bovine serum (FBS) (95 µl) and then left to stand on ice for 1 hour. After washing with PBS, fluorescence intensity was measured using FACSCalibur (Becton, Dickinson and Company). Meanwhile, a procedure similar to the above was performed using the control antibody prepared in (1) above instead of the polyclonal antibody against MCEMP1, so that a control was prepared. As a result, fluorescence intensity was found to be at least 30% stronger in all cells to which the anti-human MCEMP1 antibody had been added than that in control cells. Specifically, the following increases in fluorescence intensity were confirmed: U937: 175%, THP-1:

123%, and MDS92: 137%. Based on the above, it was confirmed that the MCEMP1 protein was expressed on the cell membrane surfaces of the above human cancer cell lines.

In addition, the rate of increase in fluorescence intensity is represented by the rate of increase in mean fluorescence intensity (MFI value) in cells. It was calculated by the following equation.

Rate of increase in mean fluorescence intensity (rate of increase in fluorescence intensity)(%)=((MFI value of cells reacted with an anti-human MCEMP1 antibody)–(control MFI value))/(control MFI value)×100

Example 4: Antitumor Effects (ADCC Activity) of Polyclonal Antibody Against MCEMP1 to Cancer Cells Next, it was examined whether or not a polyclonal antibody against MCEMP1 would be able to damage MCEMP1-expressing tumor cells. Evaluation was carried out using the polyclonal antibody against human MCEMP1 prepared in Example 3. A human leukemia cell line U937 and a myelodysplastic syndrome cell line MDS92 ($10^6$ cells each), in which MCEMP1 expression had been confirmed, were separately collected into a 50-ml centrifugal tube. Chromium 51 (100 µCi) was added thereto, followed by incubation at 37° C. for 2 hours. Thereafter, cells were washed 3 times with an RPMI1640 medium containing 10% fetal bovine serum and added to wells ($10^3$ cells per well) in 96-well V-bottom plates. The above polyclonal antibody against human MCEMP1 was added thereto (1 µg per well). Further, lymphocytes separated from mouse peripheral blood were added thereto ($2×10^5$ cells per well), followed by culture under conditions of 37° C. and 5% $CO_2$ for 4 hours. After culture, the level of chromium (Cr) 51 released from damaged tumor cells in each culture supernatant was determined. Then, the ADCC activity of the polyclonal antibody against human MCEMP1 to cancer cells was calculated. As a result, ADCC activities against the U937 cells (18.1%) and the MDS92 cells (17.3%) were confirmed (see FIG. 4). Meanwhile, substantially no activity against each cell line was observed in a case in which a procedure similar to the above was performed using the control antibody prepared from peripheral blood of a mouse that had not been immunized with an antigen (Example 3) or in a case in which no antibody was added (see FIG. 4). Accordingly, it was revealed that MCEMP1-expressing tumor cells can be damaged by inducing the ADCC activity with the use of an antibody against MCEMP1.

Figure 4:
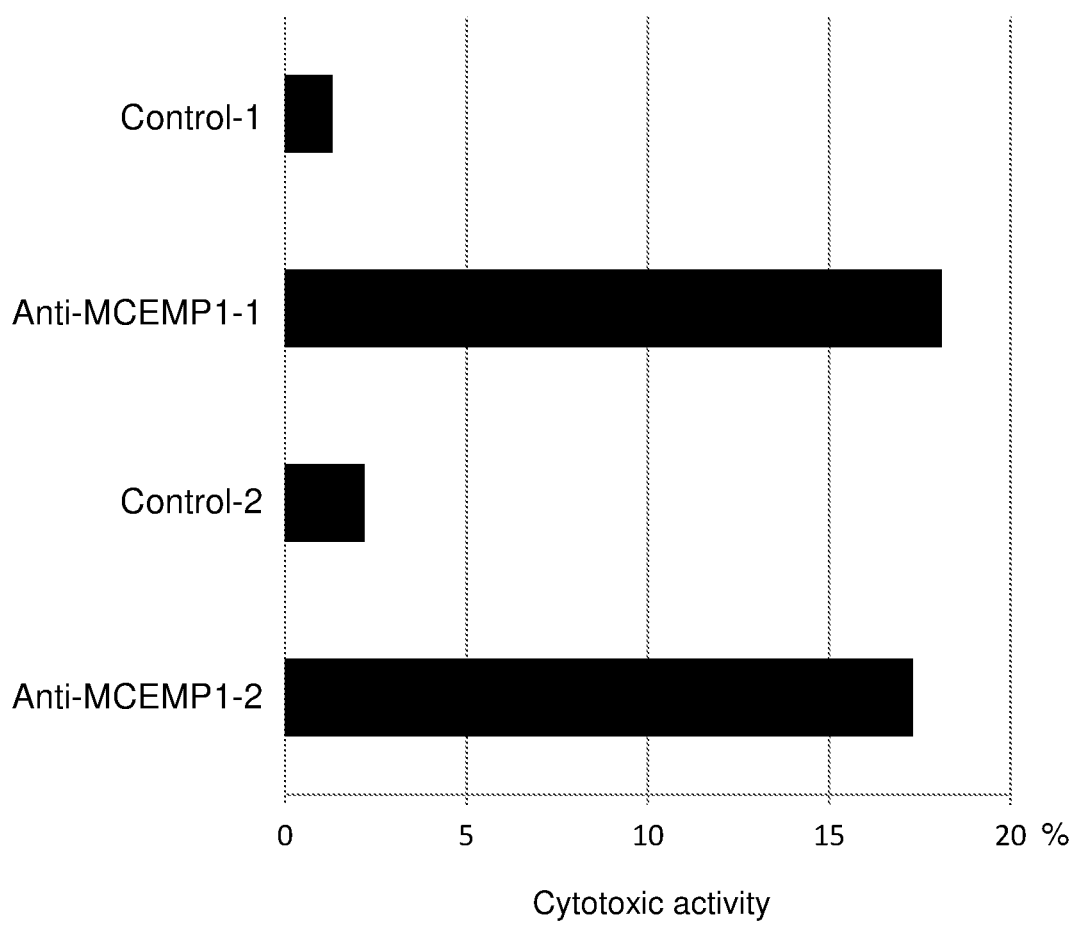
FIG. 4 shows the cytotoxic activity of polyclonal antibodies to MCEMP1 (anti-MCEMP1 polyclonal antibody) against the leukemia cell line (U937) and the myelodysplastic syndrome cell line (MDS92) expressing MCEMP1 gene. In this figure, Control-1 shows the cytotoxic activity against the U937 cells after addition of a control polyclonal antibody, Anti-MCEMP1-1 shows the cytotoxic activity against the U937 cells after addition of the anti-MCEMP1 polyclonal antibody. Control-2 shows the cytotoxic activity against the MDS92 cells after addition of the control polyclonal antibody, MCEMP1-2 shows the cytotoxic activity against the MDS92 cells after addition of the anti-MCEMP1 polyclonal antibody.

In addition, for cytotoxic activity (ADCC activity) in FIG. 4, an antibody against MCEMP1 used in the present invention, mouse lymphocytes, and $10^3$ cells of the above cell lines incorporating chromium 51 were mixed together and cultured for 4 hours, and then the level of chromium 51 released into the medium was determined as described above. Then, the cytotoxic activity to the leukemia cell line was calculated by the following equation*.

*Equation: Cytotoxic activity (%)=[(the level of chromium 51 released from U937 to which an antibody against MCEMP1 and mouse lymphocytes were added)/(the level of chromium 51 released from target cells to which 1 N hydrochloric acid was added)]×100

INDUSTRIAL APPLICABILITY

The antibodies of the present invention are useful for treatment and/or prevention of cancers.

All publications, patents, and patent applications cited herein are incorporated herein by reference in their entirety.

The invention claimed is:

1. A method of treating a cancer, said method comprising administering a pharmaceutical composition to a subject in need thereof, wherein said pharmaceutical composition comprises as an active ingredient, a polyclonal antibody specifically binding to a polypeptide consisting of the amino acid sequence of SEQ ID NO: 10 and has an antibody dependent cellular cytotoxicity (ADCC) activity, and wherein said cancer is a cancer expressing MCEMP1 on the cell surface and said cancer is leukemia or myelodysplastic syndrome.

2. The method according to claim 1, further comprising administering a second pharmaceutical composition comprising an antitumor agent to the subject.

* * * * *